(12) United States Patent
Kim et al.

(10) Patent No.: US 7,982,098 B2
(45) Date of Patent: Jul. 19, 2011

(54) ENVIRONMENTAL STRESS RESISTANCE TRANSCRIPTION FACTOR AND METHOD FOR ENHANCING ENVIRONMENTAL STRESS RESISTANCE OF PLANTS USING THE SAME

(75) Inventors: Min-Kyun Kim, Seoul (KR); Jin-Wook Jung, Gyeonggi-do (KR); So-Youn Won, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 603 days.

(21) Appl. No.: 11/922,341

(22) PCT Filed: May 15, 2006

(86) PCT No.: PCT/KR2006/001804
§ 371 (c)(1),
(2), (4) Date: Feb. 26, 2008

(87) PCT Pub. No.: WO2006/135151
PCT Pub. Date: Dec. 21, 2006

(65) Prior Publication Data
US 2010/0186112 A1    Jul. 22, 2010

(30) Foreign Application Priority Data
Jun. 17, 2005  (KR) ........................ 10-2005-0052321

(51) Int. Cl.
*C12N 15/82* (2006.01)
*C12N 15/29* (2006.01)
*C07K 14/415* (2006.01)

(52) U.S. Cl. .... 800/289; 530/370; 536/23.6; 435/320.1; 435/252.3

(58) Field of Classification Search ........................ None
See application file for complete search history.

(56) References Cited

U.S. PATENT DOCUMENTS
2004/0098764 A1    5/2004    Heard et al.

OTHER PUBLICATIONS

GenBank Database Accession No. BQ294530, Jun. 30, 2002, Lemma/palea-enriched cDNA library from elongation stage of kernel *Hordeum vulgare* subsp. *vulgare* cDNA clone 1-290, mRNA sequence.*

Yu Z. et al. Cloning and expression of a new Tibetan hulless barley (*Hordeum vulgare*) beta-1,3-glucanase gene. Biotechnol Lett. Apr. 2003;25(8):617-22.*

Mylne, J. S. & Botella, J. R. 1998. Binary vectors for sense and antisense expression of *Arabidopsis* ESTs. Plant Molecular Biology Reporter 16: 257-262.*

Murray F. et al. Comparison of Agrobacterium-mediated transformation of four barley cultivars using the GFP and GUS reporter genes. Plant Cell Rep. Jan. 2004;22(6):397-402. Epub Oct. 3, 2003.*

Gutterson N. et al. Regulation of disease resistance pathways by AP2/ERF transcription factors. Curr Opin Plant Biol. Aug. 2004;7(4):465-71, Available online May 18, 2004.*

Yi et al., "The Pepper Transcription Factor *CaPF1* Confers Pathogen and Freezing Tolerance in *Arabidopsis*", *Plant Physiology*, 2004, pp. 2862-2874, vol. 136, American Society of Plant Biologists, Rockville, Maryland, U.S.

Aharoni et al., "The SHINE Clade of AP2 Domain Transcription Factors Activates Wax Biosynthesis, Alters Cuticle Properties, and Confers Drought Tolerance when Overexpressed in *Arabidopsis*," *The Plant Cell*, 2004, pp. 2463-2480, vol. 16, American Society of Plant Biologists, Rockville, Maryland, U.S.

Gutterson et al., "Regulation of disease resistance pathways by AP2/ERF transcription factors," *Current Opinion in Plant Biology*, 2004, pp. 465-471, vol. 7, Elsevier Ltd., Oxford, England.

* cited by examiner

*Primary Examiner* — Cynthia Collins
(74) *Attorney, Agent, or Firm* — Buchanan Ingersoll & Rooney PC

(57) ABSTRACT

The present invention relates to a novel environmental stress-resistant transcription factor and a method for enhancing the environmental stress resistance of plants using the same. More particularly, the invention relates to an environmental stress-resistant transcription factor isolated from barley and a method for enhancing the environmental stress resistance of plants by introducing a vector comprising the transcription factor into the plants.

13 Claims, 19 Drawing Sheets

(15 of 19 Drawing Sheet(s) Filed in Color)

FIG. 1

```
HvRAF     MCGGAILAQLIPPS--AGRPSKQAAAGGRAPPTSSKKG-GVSKSRHSSTPDADDDVFEAA  57
AAK92635  MCGGAILAEFIPAPSRAAAATKRVTASHLWPAGSKNAARGKSKSKRQQRSFADVDDFEAA  60

HvRAF     FEDFDDHFDLRAEEDGGDDHVVFASKPAFSPRPAYDGGRAAHAASRKKRTGHLHGIRQRP  117
AAK92635  FEQFDDDSDFDDAEEEDEGHFVFASKSRVVAG--HDGRAAARAASKKKRGRHFRGIRQRP  118

HvRAF     WGKWAAEIRDPHKGTRVWLGTFDTADDAARAYDVAARRLRGSKAKVNFPDAARTGARPRR  177
AAK92635  WGKWAAEIRDPHKGTRVWLGTFNTPEEAARAYDVEARRLRGSKAKVNFP-ATPAAARPRR  177

HvRAF     ASRRTAQKPQCPPARTTAYSATAAARAQPEQDAMMVKPELMEFFNVDAIVHLTTAVAALP  237
AAK92635  GNTRATAVP--PPA------TAPAAAPPRGLKREFSPPAETALPFFTNGFVDLTTAAAPPP 230

HvRAF     PVTAS-TFADTMPRVDE---------------DSSVGSGGG--AMLGFADELGFDPFMMFQL  281
AAK92635  AMMMTSSFTDSVATSESGGSPAKKARSDDVDSSEGSVGGGSDTLGFTDELEFDPFMLFQL  290

HvRAF     PCSDMYESADSIFAGDAVIPDALSVDSGMDA-VSLWSFDEFPMDSAIF              328
AAK92635  PYSDGYESIDSLFAAG----DANSANTDMNAGVNLWSFDDFPIDGALF              334
```

FIG. 3

TCTATTGCTTATAATTTTAGTGGGCAACAATATCACTAATGTCCCTATTAGTGGTGAGGTGTCTACAATGAAT░░░░░TCCTAAAAGA
CTATGACTCTGGTGTTCAGTGCCCATTGTGTGTGTATGTGAGTAAATGGATTAGCTGATTAATGTTTGACACATTTTATACACAAGGTCAA
TCTACATTGGATCAAGAAAATGTTGAGAAAGAGTAAAACCCAAGGCTTATGAGTGTTGTTGTTGTTGAAGCACCCCATGCATGATTAGAGA
CAAGGAGAAAGTGTGTTATG░░░░░GATG░TTTTTTTTTAAAGGAGATGCATGCTTAGAGAAATTAAGGTTAGCTAGCCGACTAATCCTACT
AAAAGTAATACTTGATTATTGTCGTTTCAATTAAAAAAATACCTTGATTATTGCTGTTCCGGTT░░░░░ATTGGTCAAGTAATCAATCA
GTGATATCAATTAGGTTAGGCCTAACTAATACAAGTGGTCGTCCATTTCTTTCTGGGTCTAGGCTCGATCATTTGCGGAGCTGAGCCAAGT
GGCTCGCACAAGTTCATGTATCAGGAAAAAGTTGAGCTATTCACGCGGCCAAATTGTGTGTTCCTCCTT░░░░░GTTGTGCCGTGTCAT
TCGGCAGCTGACTGTTGTGTTCCTGGCTTCC░░░░░GCATCATGTGATGCCACCTCAGTTGTTGAGTCGTCCAATGTACCGGTTCCC
TGTCAACCGAGAAAATGGCTATTTGCCACTTTTAATATTGGCTTCTC░░░░░CTCTCAAGATTGGTTTCGTAAAAATGTCATCC
AACCCATGTGTACTT░░░░░TC░░░░░CTTTTTCAATGCTTTGCTTTTTCTTTTC░░░░░AACATCTGAAGGGACCAAT
ATACCCCTAGCCTATGCACATGTACTAGTTTTTTGCATCCAACTTGAAACAACGCCGTTGAGCGCCCGCCGTCGGCCGAGATCACCGCATA
CAGTTCGCCAAGCCCTCCTCTGGTCCTCCCCCATGATCCATCAGCTCTTCTACCTGCACATTGTAGGGCTGCTCCTGCTTGCCGATTGCTT
GGAAGTGGGCTGCCGATTGGCTGGAC░░░░░ACAGGTTGCCTGGACGCCATGCGGCCCACGCGCCTCTTATCGACACTCTGCGTCAT
CTATCTCTAGGTATCGCAGTGGAATGAACTCAATCCTTCTACACAGTATTCTTCTATCTGTACCTTCGAATATG░░░░░GTGTTAA
CCTGCACATCAGAGACAACTAGTAGAAGTATACAAGGGAAATTTTAGAATATGTAAATTCTATTCTGCATGGTTCATTTAGAA░░░░░A
TGTTCTCCTACAACTTGATGATTTGTTCTACCTTGGTGGTGTTATGTACATGTCATTGATACC░░░░░TCAGGCAAACTGTAGCCGAA
TCTTCTGAATATATGTTCAACAATATGAAAATGAGAAGCAAGTGT░░░░░TGTATAACACACATACATGCAGACGCCTTGCTTTCT
TGTTGGGAGAGGATACATCTTCACAAGCAACAACAACAACTACAGAGGATGTCCACTACAGCTCCAACAAAGAAGTTGACTCCAAAAGAA
AGCTAAAA░░░░░TGGATGAACGATCTCTACGAAATTGATGCTATAGTTATTTGAGGAAGTTGAATACTCCCTTCGTTAATAAACTTG
AACATCTAGGTTACCTGCATGTTCCTGCCTCACCTCTCTAGCATGTCACACGACGAGCTGCGCTAGCGCACATGCACGGATGAGCTGCGGT
TGCTCGCGGGCATGGCCGGCAAGCTATACGACGGCTCGTGCAAATGTGGACGAGCAC░░░░░CGAGCTCCGCCGTCGCGCACAGGCTTGG
GTGAG░░░░░TGGGTGGTGGCGAACTGCAGTTGCTGGTGCAGGCGTTGGCAAGCTAGGGCGGCGAGCTGCGATGCCTCGCACTGGCATCA
GCGAGCTACGGGCGACGGGCTTTGGTGGAGAACGAAACACCTCACAGACCCAACCAATCCACACAGGCGTGAGATAAGGTTGAATTATCCAG
GGGTATTTTGGTCCCTTCAGGTGCCAGGAAATGGAAAAGAAAAG░░░░░AAAAAAGAGAAAATGGCATGTTAATCAAAGTGCAAT
CAAACTGAGTGGCACTTTTACGCAGCCAATCTTAAGAGTGGCAATTTTGAGAAGCCGAGTATTGAAAATGGTAAATAACCAATTTTCTCCT
GCCAACCACACGACACACACGATCGTCTTGGTCAGCTAGCTTGCGTTTATAAGTAGGCGCAGCTCCGTCTCTCGGTGACCAACACAAGACG
TGAGAGAAGAAAGCGCGAGACAGGAAGATAAAACA<u>ATG</u>

Wild-type    HvRAF-overexpressed    HvRAF-overexpressed
             plant #4               plant #6

ENVIRONMENTAL STRESS RESISTANCE TRANSCRIPTION FACTOR AND METHOD FOR ENHANCING ENVIRONMENTAL STRESS RESISTANCE OF PLANTS USING THE SAME

TECHNICAL FIELD

The present invention relates to a novel environmental stress-resistant transcription factor and a method for enhancing the environmental stress resistance of plants using the same. More particularly, it relates to an environmental stress-resistant transcription factor isolated from barley and a method for enhancing the environmental stress resistance of plants by introducing a vector comprising the transcription factor into the plant.

BACKGROUND ART

Various environmental stresses, such as plant pathogenic microorganism, drought, high-concentration salt, low temperature and high temperature, act as factors that suppress the growth of plants and limit the production of crops in many important agricultural fields. It is known that *Ralstonia solanacearum*, one of plant pathogenic microorganism, penetrates the roots of plants and clogs the vessels so as to suppress water supply, thus withering the leaves of the host plants (Vasse et al., Mol. Plant-Microbe Interact, 8:241-251, 1995; Wallis et al, Physiol. Plant Pathol, 13:307-31, 1978). Those known to be main host plants of *Ralstonia solanacearum* include about 450 important crops, including tropical crops, subtropical crops and cereals, such as tomato, potato, tobacco plant, banana and olive (Hayward, Annu. Rev. Phytopathol, 29:65-87, 1991).

Also, when plants are exposed to environmental stresses, such as high-concentration salt, high temperature, low temperature and drought, osmotic imbalance and ionic imbalance in the plant cells will occur, and so the growth and photosynthesis of plants will be suppressed.

Meanwhile, plants have evolutionally developed defense mechanisms against such environmental stresses. Typical example of defense mechanisms against plant pathogenic microorganism include the synthesis of plant hormones, such as salicylic acid, jasmonic acid and ethylene, the synthesis of antibiotic compounds, such as phytoallexin, cell wall enforcement, and the expression of various pathogen resistance genes. Also, defense mechanisms against high-concentration salt stress include the maintenance of ion homeostasis by several transporters located in the plant cell membrane, and the activation of salt overly sensitive (SOS) signaling pathways having resistance to high-concentration salt stress (Zhu, J. K., Curr. Opin. Plant Biol, 6:441-445, 2003). Defense mechanisms against stresses, such as drought and low temperature, include mechanisms using ABA-dependent signaling pathways or ABA-independent signaling pathways (Zhu, J. K., Annu Rev Plant Biol, 53:247-273, 2002).

However, the above-described defense mechanisms against environmental mechanisms, which result from, e.g., pathogen resistance proteins, transporters, and various kinases, have species-specific or environment-specific characteristics, and thus have a shortcoming in that they cannot induce a broad spectrum of resistance (Bent, A. F., Plant Cell, 8:1757-1771, 1996).

Accordingly, many studies on methods capable of simultaneously expressing a group of relevant genes rather than individually expressing stress-resistant genes contained in plants themselves have been recently conducted. Among these studies, in particular, a study on transcription factors that regulate the expression of a group of environmental stress-resistant genes receives attention. For example, the effects of transcription factors CBF and Alfin1, which regulate a group of cold-resistant genes or salt-resistant genes, were verified, and an ethylene response element biding protein (EREBP) is known as a transcription factor that regulates the expression of a group of pathogen resistance genes. As another example, there are AP2 family transcription factors. The AP2 family transcription factors are classified into several groups, such as ethylene response factor (ERF), dehydration-responsive element-binding (DREB)/C-repeat (CRT)/DRE-binding factor (CBF) and RAV. ERF-type transcription factors bind to the GCC-box to regulate the expression of stress-responsive genes.

DISCLOSURE OF INVENTION

Technical Problem

Accordingly, the present inventors have conducted studies on methods capable of increasing the environmental stress resistance of plants, and as a result, isolated a novel environmental stress-resistant transcription gene from barley, and found that, if the isolated transcription factor was introduced and expressed in plants, the environmental stress resistance of the plants would be increased, thereby completing the present invention.

Therefore, it is an object of the present invention to provide an isolated polypeptide comprising an amino acid sequence of SEQ ID NO: 35, and an isolated polynucleotide encoding the polypeptide.

Another object of the present invention is to provide a recombinant vector comprising said polynucleotide, and transformed bacteria with the vector.

Still another object of the present invention is to provide a method for enhancing the environmental stress resistance of a plant, comprising introducing the said vector into the plant, as well as an environmental stress-resistant plant produced by said method.

Technical Solution

To achieve the above objects, in one aspect, the present invention provides an isolated polypeptide comprising an amino acid sequence of SEQ ID NO: 35, and an isolated polynucleotide encoding the polypeptide.

In another aspect, the present invention provides a recombinant vector comprising said polynucleotide, and transformed bacteria with the vector.

In still another aspect, the present invention provides a method for enhancing the environmental stress resistance of a plant, comprising introducing said recombinant vector into the plant, as well as an environmental stress-resistant plant produced by the method.

Hereinafter, the present invention will be described in detail.

DEFINITION

Unless otherwise stated, all technical and scientific terms used herein have the same meanings as commonly understood by those skilled in the art. The following references provide one skilled in the art with a general definition of various terms and expression used herein: Singleton et al., DICTIONARY OF MICROBIOLOGY AND MOLECULAR BIOLOGY (2d ed. 1994); THE CAMBRIDGE DIC- TIONARY OF SCIENCE AND TECHNOLOGY (Walker ed., 1988); and Hale & Marham, THE HARPER COLLINS DICTIONARY OF BIOLOGY.

As used herein, the term "environmental stress" refers to external factors that suppress the growth or production of plants, and the environmental stresses are broadly divided into biotic stresses and abiotic stresses. The biotic stresses may typically include pathogenic microorganism, and the abiotic stresses may include drought, high-concentration salt, low temperature, high temperature and oxidative stress.

As used herein, the term "environmental stress resistance" refers to a characteristic in that a reduction in the growth or production of plants, caused by the above environmental stresses, is inhibited or delayed.

As used herein, the term "environmental stress-resistant transcription factor" refers to a protein or a gene encoding the protein, the expression of which is induced by the above-described environmental stresses to show the activity to induce the expression of genes associated with defense mechanisms against the environmental stresses. The genes associated with defense mechanisms against the environmental stresses include a group of biotic stress responsive genes, including resistance (R) genes, plant defensin (PDF) genes, and pathogen-related (PR) genes, and a group of abiotic stress responsive genes, including cold-related (COR) genes, RD genes, and GSH genes. Examples of the PDF genes belonging to the biotic stress responsive gene group include PDF1.2, and examples of the PR genes include PR1 and PR5. Moreover, examples of the COR genes belonging to the abiotic stress responsive gene group include COR6.6, and examples of the GSH genes includeGSH1.

As used herein, the term "polynucleotide" refers to a nucleic acid molecule comprising a plurality of polymerized nucleotides. The polynucleotide may be, for example, genomic DNA, RNA, cDNA, PCR product, cloned DNA, synthetic DNA or RNA. The polynucleotide preferably has a nucleotide sequence encoding a polypeptide (protein), its domain or its fragment.

As used herein, the term "polypeptide" is used interchangeably with "peptide" or "protein", and refers to, e.g., a polymer of amino acid residues.

As used herein, the term "expression vector" means a plasmid, virus or other vehicle known in the art that has been manipulated by inserting or introducing of the polynucleotide sequence of the present invention.

As used herein, the term "operably linked" may mean that a polynucleotide is linked to an expression control sequence in such a manner to enable expression of the polynucleotide when a suitable molecule is bound to the expression control sequence.

As used herein, the term "expression control sequence" means a DNA sequence that regulates the expression of the operably linked nucleic acid sequence in a certain host cell.

The present invention is based on a novel gene HvRAF encoding a protein of the putative AP2/ERF transcription factor family was isolated from a barley cDNA library, and the characteristics of the isolated gene were identified.

To isolate the environmental stress-induced AP2/ERF genes in barley, the present inventors selected an EST clone from the Institute for Genomic Research (TIGR) Barley Unique database and screened the barley cDNA library using the EST clone as a probe. As a result, a partial gene with 734 bp size was screened and full-length cDNA of the partial gene was prepared by RT-PCR using total RNA from barley seedlings as a template with the sense primer matching the 5' end of the barlery EST and the antisense primer matching the 3' end of the isolated partial gene (see Example <1-1>).

The sequence of the cDNA was analyzed, and as a result, it could be found that the cDNA has 984 nucleotides (SEQ ID NO: 3) encoding 328 amino acids (SEQ ID NO: 4). The barley-derived cDNA had about 45% sequence homology to the putative AP2/ERF transcription factor derived from rice, and the conserved AP2ERF DNA-binding domain had about 90% sequence homology (see Example <1-2> and FIG. 1). Thus, it was inferred that the above-described cDNA would be a novel transcription factor of the AP2/ERF family.

Furthermore, in order to select a promoter that regulates the gene from barley, the present inventors obtained the base sequence of the whole genome gene (SEQ ID NO: 23) by BAC clone library screening and chromosome working using the barley-derived gene as a probe, and obtained a promoter sequence (SEQ ID NO: 24) located upstream of the translation initiation codon (see Example 2).

Moreover, the present inventors performed Southern blot analysis of genomic DNA extracted from barley (see Example 3) and found that the gene exists as a single copy (see FIG. 4). Also, the expression pattern of the gene was examined by Northern blot analysis (Example 4), and as a result, it was found that the gene according to the present invention has a characteristic in that it is expressed at a relatively higher level in roots than in other tissues (see FIG. 5). Thus, the present inventors named said gene "HvRAF" (Hordeum v ulgare R oot A bundant AP2/ERF Transcription F actor). Also, it was found that the HvRAF gene has a characteristic in that it is expressed at higher levels in dark growth conditions than in long-day conditions (see FIG. 6).

Furthermore, in order to confirm whether said gene actually functions as a transcription factor, the present inventors analyzed the nuclear migration of said gene by nuclear migration test in *Arabidopsis thaliana* protoplasts (see Example 5 and FIG. 7), and prepared deletion mutants of said gene to identify a region (having an amino acid sequence of SEQ ID NO: 35 and a base sequence of SEQ ID NO: 36) involved in transcriptional activity (see Example 6 and FIG. 9).

In order to confirm the functions of the HvRAF gene, the present inventors examined whether the expression of said gene is induced by various environmental stresses (see Example 7).

As a result, it could be found that the expression of the inventive HvRAF gene is induced by treatment with plant hormones induced by plant hormones such as salicylic acid, ethephon and methyl jasmonic acid as well as wounding. In addition, the expression of the HvRAF gene was induced by treatment with cellulase or methyl viologen (MV; paraquat), a pesticide component that induces oxidative stress (see FIGS. 10 and 11). From this result, it was presumed that, since the HvRAF gene according to the present invention has a characteristic in that it is induced by various stresses, the gene would be associated with action to defend stresses.

To confirm this presumption, the present inventors produced *Arabidopsis thaliana* where the HvRAF gene is overexpressed, and we examined the resistance of the produced *Arabidopsis thaliana* plant to environmental stresses, such as pathogen and high-concentrations of salt. Also, we examined whether the overexpression of the HvRAF gene in *Arabidopis thaliana* induces the expression of pathogen resistance genes and low-temperature-resistant genes (see Example 8).

As a result, it could be found that the HvRAF gene isolated from barley, a monocotyledon, can perform defense mechanisms against pathogenic microorganism and high-concentration salt even in *Arabidopsis thaliana*, a dicotyledon (see FIGS. 13, 14, 15 and 16), and the HvRAF gene overexpressed in *Arabidopsis thaliana* induces the expression of pathogen resistance genes and low-temperature-resistant genes (see FIG. 17).

Also, in tests by the present inventors, seeds harvested from the HvRAF gene-overexpressed *Arabidopsis thaliana* plant were sowed in a medium containing a high concentration of ABA (abscisic acid) or salt, and the germinability of the harvested seeds was measured (see Example 9). The ABA and salt are typical factors that inhibit germination by affecting various physiological actions and signaling mechanisms occurring in seeds. As a result, it could be found that, in the case of the HvRAF gene-overexpressed seed, germination is not inhibited by a high concentration of ABA and salt (see FIGS. 18 and 19). The above test results suggest that the inventive HvRAF gene can also enhance the environmental stress resistance of plant seeds.

Accordingly, the present invention provides an isolated polypeptide comprising an amino acid sequence of SEQ ID NO: 35. Preferably, the polypeptide consists essentially of the amino acid sequence of SEQ ID NO: 35. And the polypeptide may be one isolated from barley and having transcription factor activity.

More preferably, the inventive polypeptide may be either a polypeptide having an amino acid sequence of SEQ ID NO: 4 or a functional equivalent of the polypeptide. As used herein, the term "functional equivalent" refers to a polypeptide that shows substantially identical physiological activity as a polypeptide set forth in SEQ ID NO: 4 and has a sequence homology of at least 70%, preferably at least 80%, and more preferably at least 90% to the amino acid sequence of SEQ ID NO: 4, as a result of the addition, substitution or deletion of amino acids. Homology or identity with respect to this sequence is defined herein as the percentage of amino acid residues in the candidate sequence that are identical with the amino acid sequence of SEQ ID NO 4, after aligning the sequence and introducing gaps, if necessary, to achieve the maximum percent sequence identity, and not considering any conservative substitutions (as described above) as part of the sequence identity. None of N-terminal, C-terminal, or internal extensions, deletions, or insertions into the amino acid sequence of SEQ ID NO 4 shall be construed as affecting sequence identity or homology. Thus sequence identity can be determined by standard methods that are commonly used to compare the similarity in position of the amino acids of two polypeptides. Using a computer program such as CLUSTALW, BLAST, FASTA, GAP, BESTFIT and TFASTA in the Wisconsin Genetics Software Package, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3, 1978) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

As used herein, the term "substantially identical physiological activity" means an activity that causes the expression of the polypeptide to be induced in plants by environmental stresses so as to induce the expression of genes associated with environmental stress resistance, such that the plants have environmental stress resistance.

The polypeptide according to the present invention may be isolated from nature (e.g., plant cells) or obtained through a genetic engineering technique by the expression of a recombinant nucleic acid encoding the inventive polypeptide, or through chemical synthesis. Particularly preferably, the inventive polypeptide can be isolated from barley. For example, the inventive polypeptide can be prepared through a genetic engineering method comprising the steps of: inserting a polynucleotide sequence or its fragment encoding the inventive polypeptide into a vector containing one or more expression control sequence which is operatively linked to the polynucleotide sequence so as to control the expression of the polynucleotide; transforming a host with the resulting recombinant expression vector; culturing the transformed host in a medium and condition suitable to express the polynucleotide sequence; and isolating and purifying an essentially pure protein from the culture medium.

The isolation and purification of the recombinant protein can be performed using any method known in the art. For example, the recombinant protein can be isolated and purified by any method known in the art, such as extraction, recrystallization, various chromatography techniques (gel filtration, ion exchange, precipitation, adsorption and reverse phase), electrophoresis, and counter current distribution, with the reverse-phase high-performance chromatography being most effective.

In another aspect, the present invention provides an isolated polynucleotide encoding said polypeptide. Preferably, the inventive polynucleotide may comprise a base sequence represented by SEQ ID NO: 36, which is a region showing transcription activity. More preferably, the inventive polynucleotide may have a base sequence set forth in SEQ ID NO: 3, which is a full-length cDNA sequence. Also, the inventive polynucleotide may consist of a base sequence of SEQ ID NO: 23, which is a genomic gene comprising both a promoter region and a coding region.

The polynucleotide according to the present invention encodes a transcription factor of a subclass of Class IV, which contains the DNA-binding domain of a typical AP2/ERF transcription factor (Tournier et al., FEBS Lett, 550:149-154, 2003). The inventive polynucleotide has tissue specificity in that it is expressed at a higher level in the plant roots than in other tissues. Also, the inventive polypeptide has a characteristic in that its expression is induced at higher level in dark condition than in long-day condition.

In still another aspect, the present invention provides about 4-kb promoter that control the expression of the inventive HvRAF gene. The promoter may be comprised of a base sequence of SEQ ID NO: 24. This promoter contains various cis-elements that induce stresses.

The polynucleotide according to the present invention can be inserted into a suitable expression vector to transform plant cells. Accordingly, the present invention provides a recombinant vector comprising the inventive polynucleotide. The polynucleotide sequence according to the present invention can be operably linked to an expression control sequence, and the polynucleotide sequence operably linked to the expression control sequence can be included in a single expression vector containing both a selection marker and a replication origin. The expression control sequence includes a promoter for performing transcription, an optional operator sequence for controlling transcription, a sequence encoding a suitable mRNA ribosome-binding site, and a sequence controlling termination. Vectors suitable to introduce the inventive polynucleotide into plant cells include a Ti plasmid, a root-inducing (Ri) plasmid and a plant virus vector. Examples of the suitable vectors include, but are not limited to, binary vectors, such as pPZP, pGA and pCAMBIA series. Anyone skilled in the art can select a vector suitable to introduce the polynucleotide sequence of the inventive gene. In one embodiment of the present invention, a recombinant vector was prepared by inserting the inventive polynucleotide into the XabI and XhoI restriction enzyme sites of plant binary vector pBI111L.

The introduction of said recombinant vector into plants can be performed using any method known in the art. Examples of the method for introducing the recombinant vector include, but are not limited to, *Agrobacterium* species-mediated transformation, particle gun bombardment, silicon carbide whiskers, sonication, electroporation and PEG (polyethyleneglycol) precipitation. In one embodiment of the present invention, *Arabidopsis thaliana*. was transformed with the inventive recombinant vector using the *Agrobacterium* species-mediated transformation.

Thus, the present invention provides host cells transformed with the inventive recombinant vector. The host cells are preferably bacteria, examples of which include *E. coli* and *Agrobacterium* sp.

In still another aspect, the present invention provides a method for enhancing the environmental stress resistance, comprising introducing into a plant of recombinant vector comprising the inventive polynucleotide.

In the inventive method for enhancing the environmental stress resistance of a plant, the environmental stress-resistant transcription factor of the present invention is introduced into either plants containing or not containing the inventive environmental stress-resistant transcription factor, so that, when the plants are subjected to environmental stresses, the expression of the transcription factor will be induced, and so the expression of a gene group associated with defense mechanisms against the environmental stresses will be induced, thereby enhancing the environmental stress resistance of the plants or imparting a new environmental stress resistance character to the plants.

The introduction of the inventive gene into plants can be performed by, e.g., a method of transforming the plants with a recombinant vector comprising the gene which is controlled by a promoter. The promoter is not specifically limited as long as it can express the gene inserted into plants. Examples of the promoter include, but are not limited to, the promoter (SEQ ID NO: 24) of the HvRAF gene isolated from barley; the 35S RNA and 19S RNA promoters of CaMV; full-length transcript promoter from a figwort mosaic virus (FMV); and the coat protein promoter of TMV. Alternatively, an ubiquitin promoter may be used to overexpress the gene in a monocotyledon or a woody plant.

In still another aspect, the present invention provides an environmental stress-resistant plant introduced with a recombinant vector comprising the inventive polynucleotide.

More specifically, the environmental stress-resistant plant according to the present invention can be obtained by transforming plants with a recombinant vector comprising the inventive polynucleotide and then subjecting the plant to the processes of callus induction, rooting and soil acclimatization according to a conventional method. Namely, the explants of the plant transformed with the recombinant vector comprising the inventive gene are placed in a suitable medium known in the art and then cultured in suitable conditions to induce the formation of calluses. When the shoots are formed, these shoots are transferred and cultured in a hormone-free medium. After about 2 weeks, the shoots are transferred to a rooting medium to induct rooting. The induced roots are transplanted and acclimated to soil, thus producing environmental stress-resistant plants.

In yet another aspect, the present invention provides a plant cell or seed which can be obtained from the environmental stress-resistant plants. The plant cell or seed have increased resistance to environmental stresses.

Plants to which the inventive method can be applied include both monocotyledon and dicotyledon. Examples of the monocotyledon include, but are not limited to, rice, wheat, barley, bamboo shoot, corn, taro, asparagus, onion, garlic, Welsh onion, leek, wild rocambole, yam and ginger. Examples of the dicotyledons include, but are not limited to *Arabidopsis thaliana*, eggplant, tobacco plant, red pepper, tomato, burdock, crown daisy, lettuce, balloon flower, spinach, chard, sweet potato, celery, carrot, water dropwort, parsley, Chinese cabbage, cabbage, radish, watermelon, melon, cucumber, pumpkin, gourd, strawberry, soybean, mung bean, kidney bean, and pea.

BRIEF DESCRIPTION OF THE DRAWINGS

The application file contains at least one drawing executed in color. Copies of this patent application with the color drawings will be provided by the Office upon request and payment of the necessary fees.

FIG. 1 shows the results of the comparison of an amino acid deduced from the base sequence of the inventive barley-derived HvRAF gene (SEQ ID NO: 4) to the deduced amino acid sequence of the AP2/ERF transcription factor from rice (GenBank accession no: AAK92635) (SEQ ID NO: 47).

FIG. 3 shows main cis elements in the promoter base sequence of the inventive HvRAF gene (SEQ ID NO: 23).
Pink: wounding responsive element (WUN element);
Yellow: salicylic acid responsive element (TCA element);
Blue: cis element associated with root-specific expression;
Gray: methyl jasmonic acid (MeJA) responsive element;
Purple: elicitor responsive element;
Sky blue: ethylene responsive element;
Green: ABA responsive element
Black: MYB binding element
Brown letter: CAAT box
Green letter: TATA box

BEST MODE FOR CARRYING OUT THE INVENTION

Figure 2:
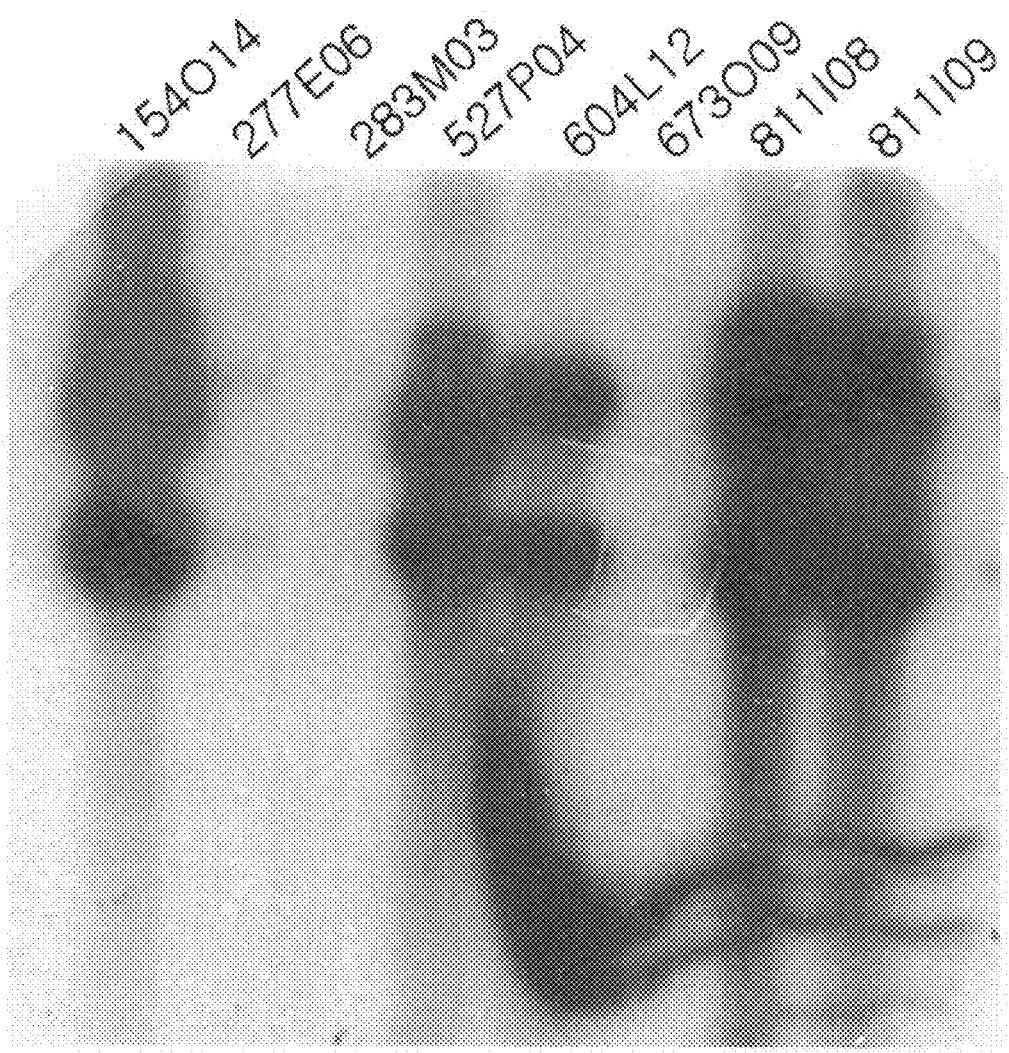
FIG. 2 shows positive clones selected from a barley bacterial artificial chromosome (BAC) clone library by Southern blot analysis.

Hereinafter, the present invention will be described in more detail with reference to the following examples. However, the examples are given for illustrative purpose only and the scope of the present invention is not limited to or by the examples.

Example 1

Cloning of Inventive HvRAF Gene

<1-1> Preparation of cDNA of HvRAF Gene from Barley Induced by Environmental Stresses To isolate the AP2/EFR gene by inducing the environmental stress, EST clones encoding either GCC- or C-repeat/DRE-binding factors were searched from the Institute for Genomic Research (TIGR) Barley Unique database. Among several candidates, TC131838 showed the highest sequence similarity to genes encoding AP2-domain containing proteins. The TC131838 is corresponded to BF256780 (846 bp in size; isolated from roots of young barley seedlings) in GenBank, which contained 141 bp longer sequence at the 3' region compared to TC131838.

To isolate the full-length cDNA of the corresponding gene, the DNA fragment of BF256780 was cloned and used as a probe to screen the barley cDNA library that had been constructed from poly(A)+RNA of 7-day-old barley seedlings. The barley cDNA library was prepared by following method. The barley seedlings grown in vermiculite soil for 7 days were treated with 200 μM of cadmium ($CdCl_2$) for 6 hours to induce the production of environmental stress-resistant mRNA which was then isolated from the tissue to prepare a cDNA library. Namely, from the barley seedling tissue treated with cadmium, total RNA was extracted using the RNeasy Plant Mini kit (Qiagen), and then from the total RNA, mRNA was extracted using the Promega mRNA isolation kit. Using the extracted mRNA as a template, cDNA was prepared with a cDNA synthesis kit (Stratagene) according to the manufacturer's protocol. Then, the cDNA was ligated with an adaptor containing a restriction enzyme EcoRI site and digested with the same restriction enzyme. The digested cDNA was fused to the same site of a pGAD424 vector (Clontech) containing a GAL4 activation promoter and then transformed into yeast YM4271 by a PEG method. The transformed yeast was plated on a medium containing 200 μM of cadmium, and then several colonies showing resistance to cadmium were selected. To select recombinant plasmids from yeast, each of the selected colonies was inoculated into an SD/-Leu medium (Clontech) containing 200 μM cadmium and then cultured at 30° C. at 250 rpm for about 20 hours. The suspended media were centrifuged at 3000 rpm for 5 minutes, and the remaining pellets were mixed with 200 μl of a lysis buffer (2% triton X-100, 1% SDS, 100 mM NaCl, 10 mM Tris-HCl, 1 mM EDTA, pH 8.0). To each of the mixtures, the same amount of acid-washed glass beads and phenol were added and the resulting mixtures were strongly vortexed. Each of the vortexed mixtures was centrifuged at 14000 rpm for 10 minutes, and then recombinant plasmids were isolated from the mixtures by ethanol precipitation. The isolated plasmids were transformed into *E. coli* by electroporation and then cultured. From the *E. coli* cultures showing antibiotic resistance, recombinant plasmids were isolated using an extraction kit (Qiagen).

As a result, partial cDNA with 734 bp size was screened, which contains polyadenylation sequences, showed a 186 by sequence overlap at its N-terminus region with the C-terminus of the EST clone.

To prepare the full-length cDNA of the partial gene, reverse-transcription PCR was performed with a One-step RT-PCR kit (Qiagen, Hilden, Germany) using 500 ng total RNA as a template. Amplification was preformed with the sense primer (SEQ ID NO: 1) matching the 5' end of the barley EST, BF256780 and the antisense primer (SEQ ID NO: 2) matching the 3' end of the isolated partial cDNA fragment. Also, the RT-PCR amplification conditions were as follows: reverse transcription of 30 min at 50° C.; transcriptase inactivation and taq polymerase activation of 15 min at 95° C.; and then 35 cycles of 30 sec at 94° C., 30 sec at 63° C. and 1 min at 72° C.

```
Sense primer HvAP2-F
5'-CAGGAAGATAAAACAATGTGT-3'     (SEQ ID NO: 1)

Antisense primer HvAP2-R
5'-GATCAATTCGTAGGACTATTG-3'     (SEQ ID NO: 2)
```

The resulting PCR amplification products were separated on a 1% agarose gel and eluted with an Accuprep Gel Purification kit (Bioneer, Yunsung, Korea) to obtain a full-length cDNA containing an initiation codon.

<1-2> Sequencing and Sequence Homology Analysis for cDNA Isolated from Barley

The sequence of the cDNA prepared in Example <1-1> was determined using a DNA automatic sequencer (Perkin-Elmer, USA) and a big dye terminator sequencing kit (Perkin-Elmer, USA). The determined DNA sequence was analyzed using a sequence analysis program and an amino acid sequence was deduced from the base sequence. Also, the sequence homology between the analyzed base sequence of the inventive gene and the known base sequence of another barley-derived gene was examined using the BLAST program and the CLUSTALW program.

The test results showed that the cDNA prepared in the present invention had 984 nucleotides (SEQ ID NO: 3) and contained an open reading frame encoding 328 amino acids (SEQ ID NO: 4). Also, the amino acid sequence of the prepared cDNA showed a homology of about 45% to the putative AP2/ERF transcription factor (GenBank accession no: AAK92635) derived from rice, and a homology of about 90% to the conserved AP2/ERF DNA-binding domain (see FIG. 1). Thus, it was inferred that the inventive HvRAF gene would be a transcription factor of the AP2/ERF family.

Example 2

Isolation and Characterization of Promoter of Inventive Hv_RAF Gene

<2-1> Isolation of Promoter of HYRAF Promoter

To isolate a promoter that controls the expression of the HvRAF gene isolated in Example 1, a barley bacterial artificial clone library was screened using the HvRAF gene as a probe (Yu et al. Theor. Appl. Genet. 101: 1093-1099, 2000). The HvRAF gene probe used in the screening step was prepared by performing PCR using the full-length HvRAF cDNA (SEQ ID NO: 3) prepared in Example <1-1> as a template and the following primers. The PCR reaction was performed in the following conditions: denaturation of 3 min at 94° C.; 36 cycles of 30 sec at 94° C., 30 sec at 51° C. and 30 sec at 72° C.; and then extension of 10 min at 72° C. The prepared probe was labeled with isotope [α-32P]dCTP.

```
Sense primer HvAP2-F2
5'-ACACGATGCCGAGGGT-3'         (SEQ ID NO: 5)

Antisense primer HvAP2-R2
5'-AGTACAGAGAGGTACCG-3'        (SEQ ID NO: 6)
```

As a result of the screening, a total of eight candidate BAC clones, HV_MBa0154014, HV_MBa0283M03, HV_MBa0277E06, HV_MBa0527PO₄, HV_MBa0604L12, HV_MBa0673009, HV_MBa0811108 and HV_MBa0811109 were selected. The candidate clones were subjected to Southern blot. For this purpose, each of the above-selected eight BAC clones was inoculated into an LB medium containing 12.5 μg/ml of chloramphenicol and then cultured at 37° C. and 250 rpm for one day. From each of the culture media, a clone was isolated using the Plasmid maxi kit (Qiagen, Hilden), and 20 μg of the clone was digested with restriction enzymeSalI for 20 hours and then loaded onto 0.8% agarose gel. After completion of the loading, the agarose gel was precipitated in modification buffer (1.5M NaCl, 0.5N NaOH) for 30 minutes, washed with double-distilled water and precipitated in neutralization buffer (1M Tris-HCl, pH7.5, 1.5M NaCl) for 30 minutes. The agarose gel was laid upside down on 3M paper wetted with 20×SSC solution, on which a N⁺ nylon membrane (Amersham) was then laid. On the membrane, two sheets of 3M paper and about 10 cm thick paper towels were stacked, on which a 1 kg bottle was then placed, followed by blotting for one day, The nylon membrane containing each of the clones was hybridized with the HvRAF gene probe at 65° C. overnight. After completion of the hybridization, the nylon membrane was washed with primary wash buffer (2×SSC and 0.1% SDS) at 55° C. for 5 minutes and then further washed with secondary buffer (0.1× SSC) for 5 minutes. The washed membrane was sensitized to light at −70° C. for one day, and then the results were examined using a developer solution.

As a result, among said eight clones, 5 positive clones (HV_MBa0154014, HV_MBa0527PO₄, HV_MBa0604L12, HV_MBa0811108 and HV_MBa0811109) were finally selected (see FIG. 2), and a promoter region containing the HvRAF gene was selected using as the HV_MBa0811108 clone as a template with the universal genome walker kit (Clontech).

More specifically, the BAC clone HV_MBa0811108 was digested with EcoRV and then ligated to an adaptor using T4 DNA ligase. PCR amplification was performed using the resulting clone as a template with sense primer AP1 (SEQ ID NO: 7) and antisense primer GSP1 (SEQ ID NO: 8). Also, the PCR amplification conditions were as follows: denaturation of 5 min at 95° C. for 5 min; 7 cycles of 30 sec at 95° C. and 4 min at 70° C.; 30 cycles of 30 sec at 95° C. and 4 min at 65° C.; and then extension of 7 min at 65° C. The PCR amplification product was electrophoresed to confirm two bands.

The PCR amplification product was diluted 50-fold, and nested PCR was performed using the diluted product as a template with sense primer AP2 (SEQ ID NO: 9) and antisense primer GSP2 (SEQ ID NO: 10). The PCR amplification product was electrophoresed, and the detected PCR band was gel-eluted and then ligated to a pGEMT-easy vector (Promega), followed by transformation into E. coli. The transformed E. coli strains were cultured in LB media containing antibiotic ampicillin, and a bacterial strain showing antibiotic resistance was selected.

Colony picking PCR was performed using the above-selected E. coli strain with sense primer T7 (SEQ ID NO: 11) and antisense primer SP6 (SEQ ID NO: 12). The PCR amplification was performed in the following conditions: denaturation of 5 min at 95° C.; 30 cycles of 30 sec at 95° C., 30 sec at 50° C. and 4 min at 72° C.; and then extension of 7 min at 72° C. The PCR amplification product was electrophoresed to confirm about 2-kb band. The sequence of the band was determined using a DNA automatic sequencer (Perkin-Elmer, USA) and a big dye terminator sequencing kit (Perkin-Elmer, USA) and then analyzed with a sequence analysis program. As a result, it was found that the band contained the HvRAF gene sequence.

Furthermore, to confirm a slightly longer sequence containing the HvRAF gene, barley genomic DNA was digested with a pvuII restriction enzyme and ligated with an adaptor, followed by PCR amplification reactions. The primary PCR amplification was performed using sense primer AP1 (SEQ ID NO: 7) and antisense primer GSP3 (SEQ ID NO: 13). The primary PCR amplification product was diluted 50-fold, and the nested PCR amplification was performed using the diluted product as a template with sense primer AP2 (SEQ ID NO: 9) and antisense primer GSP4 (SEQ ID NO: 14).

The above PCR amplification product as a template was PCR-amplified using primers, Prom-1, 2, 3, 4, 5, 6, 7 and 8

(SEQ ID NOS: 15 to 22). Then, the base sequence of the amplification product was analyzed. As a result, a 5658-bp genomic gene (SEQ ID NO: 23) containing the coding region of the HvRAF gene was obtained and a 4279-bp promoter sequence (SEQ ID NO: 24) located upstream of the translation initiation codon was obtained

TABLE 1

Primers used for isolation of promoter of HvRAF gene

| Primers | Base sequences | SEQ ID NO |
|---|---|---|
| AP1 primer | 5'-GTAATACGACTCACTATAGGGC-3' | 7 |
| GSP1 primer | 5'-TGGAGAGAAGGCAGGCTTGGATGCAAA-3' | 8 |
| AP2 primer | 5'-ACTATAGGGCACGCGTGGT-3' | 9 |
| GSP2 primer | 5'-CCCGCAGGTCGAAGTGGTCATCGAAGT-3' | 10 |
| T7 primer | 5'-TAATACGACTCACTATAGGG-3' | 11 |
| SP6 primer | 5'-GATTTAGGTGACACTATAG-3' | 12 |
| GSP-3 primer | 5'-TACGTGGCAAGGAGGAACACACAATT-3' | 13 |
| GSP-4 primer | 5'-ACATGAACTTGTCGCAGCCACTTGGCT-3' | 14 |
| Prom-1 primer | 5'-CACATTTTGCACGACCCGT-3' | 15 |
| Prom-2 primer | 5'-AGTCGTCCAATGTACCGGTT-3' | 16 |
| Prom-3 primer | 5'-CTACCTGCACATTGTAGGGCT-3' | 17 |
| Prom-4 primer | 5'-CCATTACTTGTGTTAACCTGCA-3' | 18 |
| Prom-5 primer | 5'-CTCCTACAACTTGATGATTTGT-3' | 19 |
| Prom-6 primer | 5'-CCCTTCGTTAATAAACTTGAACA-3' | 20 |
| Prom-7 primer | 5'-AACTGCAGTTGCTGGTGCA-3' | 21 |
| Prom-8 primer | 5'-AACCACACGACACACACGAT-3' | 22 |

<2-2> Characterization of HvRAF Gene Promoter

The promoter isolated in Example <2-1> was analyzed using PLANTCARE and PLACE programs. As a result, in the promoter sequence, a cis-element involved in root-specific expression was found, as well as various hormone-reactive elements (see FIG. 3).

Example 3

Analysis of HvRAF Gene Present in Barley

In order to examine whether the HvRAF gene cloned in Example 1 is actually present in the barley genome whose entire base sequence is not known and to analyze the copy number of the gene, Southern blot was performed. For this purpose, barley seedlings grown in vermiculite soil for 7 days were crushed in liquid nitrogen and then left to stand in CTAB buffer (2% CTAB, 100 mM Tris-HCl, 20 mM EDTA, 1.4 M NaCl and 1% polyvinylpyrrolidone (molecular weight: 40,000; pH 8.0)) at 60° C. for 3 hours. The medium was added to and slowly mixed with the same volume of chloroform, and the mixture was centrifuged at 3000 rpm for 50 minutes. The supernatant was transferred into a fresh tube and added to about ⅔ volume of isopropanol and then centrifuged at 12000 rpm for 5 minutes. After removing the supernatant, the precipitate was washed with 70% ethanol, and to denature RNA, RNase A was added to the washed precipitate to a final concentration of 10 μg/ml, followed by culturing at 37° C. for 30 minutes. From the culture medium, genomic DNA was isolated by ethanol precipitation and digested with 10 μg of each of restriction enzymes BamHI and HindIII for 20 hours, followed by loading onto 0.8% agarose gel. Blotting and hybridization were performed in the same manner as described in Example <2-1>.

Figure 4:
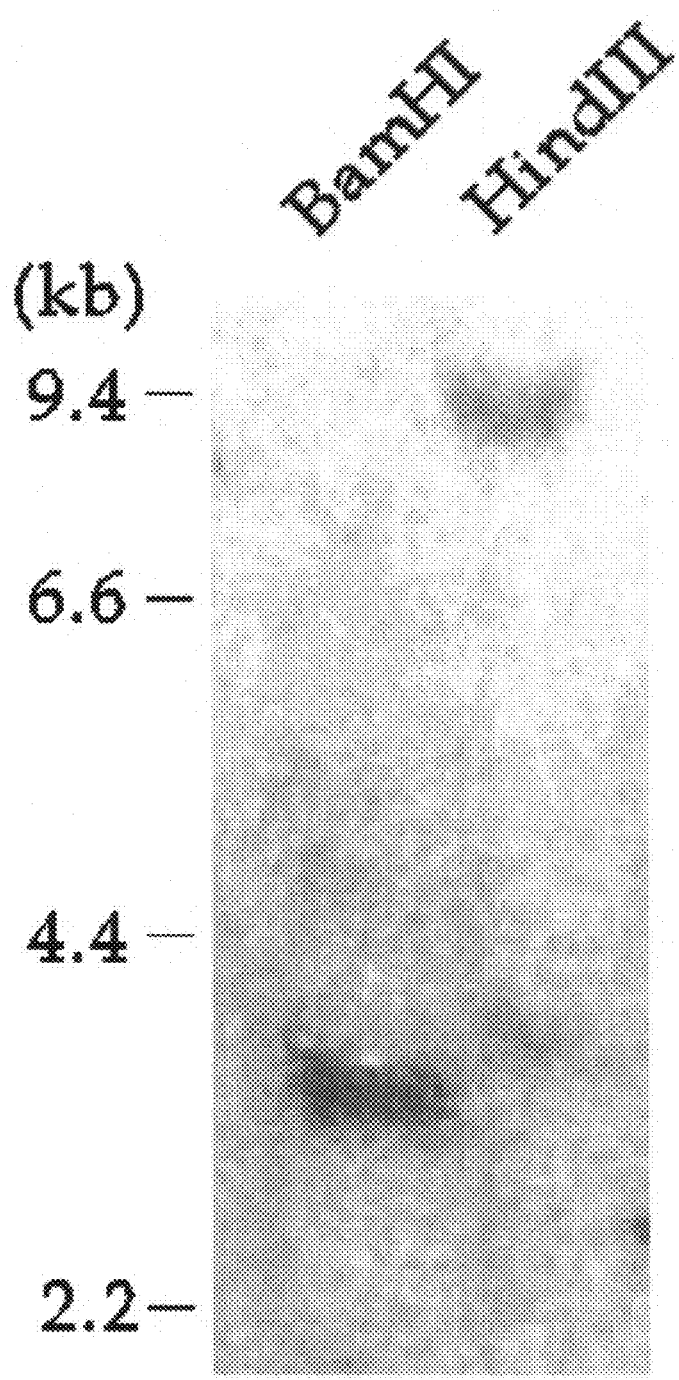
FIG. 4 shows the results of Southern blot analysis for a genomic DNA isolated from a barley seedling, conducted to determine the copy number of the HvRAF gene.

In the test results, it could be found that the inventive HvRAF gene is present as a single copy in the barley genome (see FIG. 4).

Example 4

Analysis of Expression Patterns of Inventive HvRAF Gene

<4-1> Expression Patterns According to Barley Tissues

The expression pattern of the HvRAF gene in each of barley tissues was examined by Northern blot analysis. For this purpose, from the roots, coleoptiles and leaves of barley seedlings grown in vermiculite soil for 7 days, total RNA was extracted by lithium chloride (LiCl) precipitation. In the case of the roots, the total RNA was extracted from two portions (tip and middle portions), and in the case of the leaves, the entire RNA was extracted from three portions (see FIG. 5A). 10 μg of each of the extracted total RNAs was loaded and separated on RNA agarose gel (1.2% agarose, 1×MOPS, 1.1% formaldehyde) and then transferred to a nylon membrane, followed by hybridization with the probe prepared in Example <2-1>.

Figure 5:
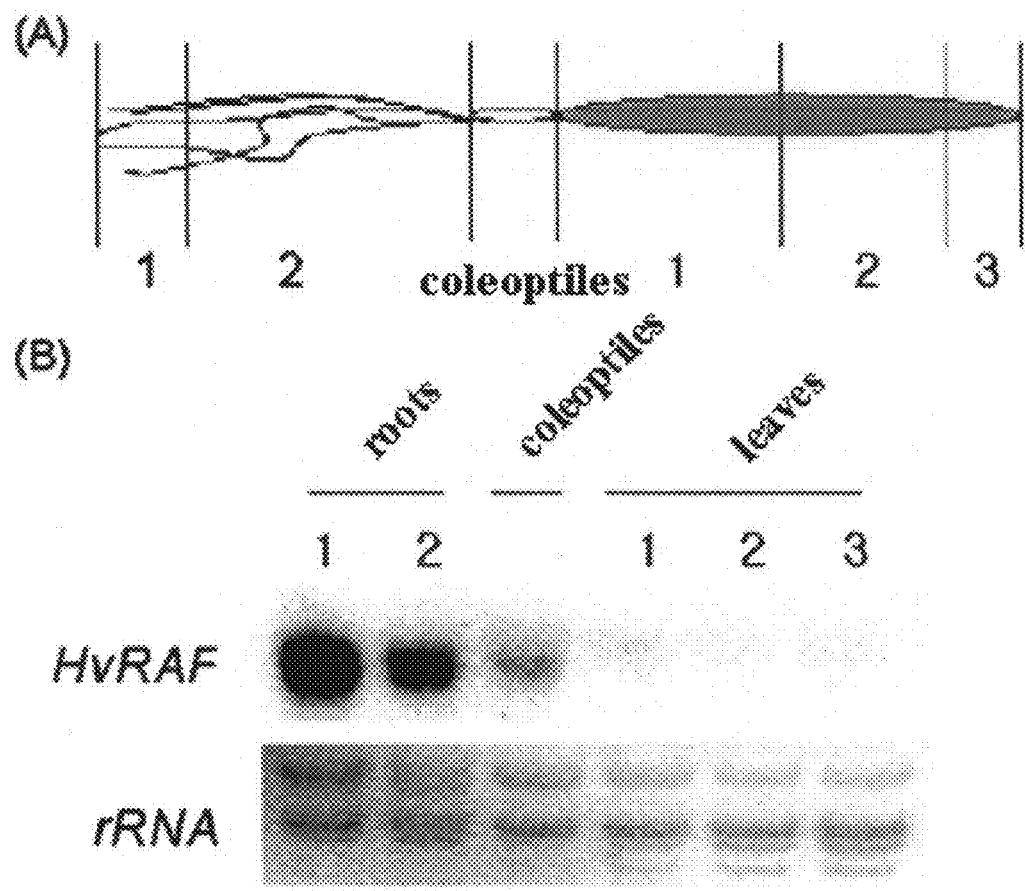
FIG. 5 shows barley tissue sections used to analyze expression patterns according to barley tissues (A), and the results of Northern blot analysis conducted to analyze the expression patterns of the inventive HvRAF gene according to barley tissues (B). rRNA was used as a loading control.

The test results showed that the HvRAF gene was expressed at a higher level in the barley roots than in the barley leaves or coleoptiles, and particularly, was expressed in the root tips which have been actively grown (see FIG. 5B). These results suggest that the expression of the HvRAF is tissue-specific.

<4-2> Expression Patterns According to Growth Conditions

The expression patterns of the HvRAF gene according to growth conditions were examined by Northern blot analysis. Barley seedlings were grown in vermiculite soil under the following growth conditions: long-day conditions for 5 days; long-day conditions for 5 days and then dark conditions for 1 day; dark conditions for 5 days; and dark conditions for 5 days and then long-day conditions for 1 day. Then, from the root of each of the barley seedlings, total RNA was extracted in the same manner as in Example <4-1>, and subjected to Northern blot analysis.

Figure 6:
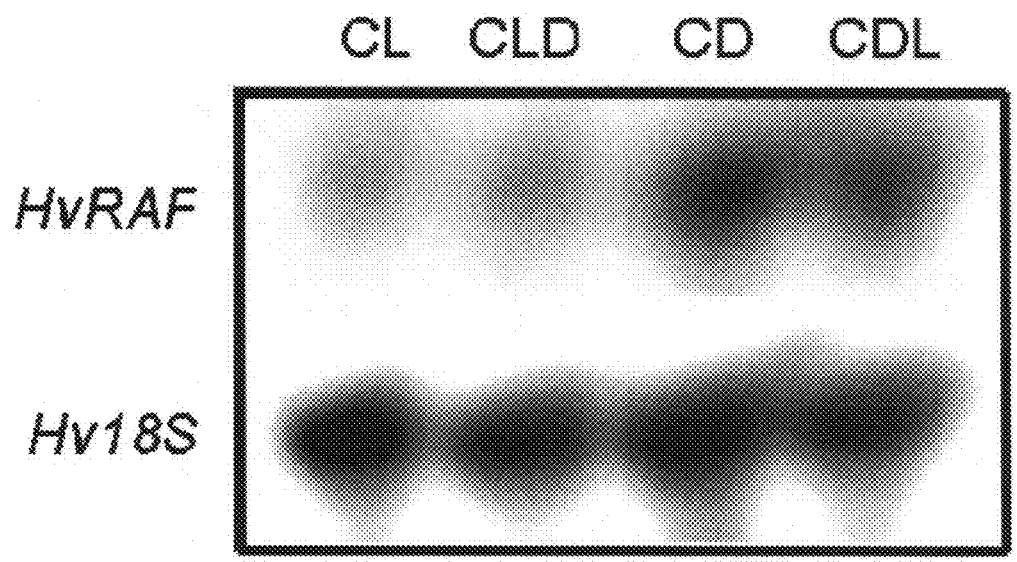
FIG. 6 shows the results of Northern blot analysis conducted to analyze the expression patterns of the inventive HvRAF gene according to the growth conditions (CL: long-day conditions; CLD: long-day conditions followed by dark conditions; CD: dark conditions; and CDL: dark conditions followed by long-day conditions). Hv18S was used as a loading control.

The test results showed that the HvRAF gene was expressed at a higher level in the root of the seedling grown under the dark conditions than in the root of the seedling grown in the long-day conditions. Also, the gene was expressed at a higher level in the seedling root grown under the long-day condition after dark conditions than in the seedling root grown under the dark conditions after long-day conditions (see FIG. 6).

Example 5

Examination of Nuclear Migration of HvRAF Gene

The transcription factor is a protein that recognizes the promoter of the relevant gene in vivo to aid the function of RNA polymerase. In order to examine whether a protein expressed from the HvRAF gene isolated from barley migrates into the nucleus and functions as a transcription factor, the HvRAF gene was transformed into the protoplasts of *Arabidopsis thaliana* and subjected to subcellular localization assay.

For this purpose, protoplasts were first isolated from *Arabidopsis thaliana*. The leaves of *Arabidopsis thaliana* grown for 5 weeks were cut into a size of 0.5-1 mm and precipitated in a solution containing cellulase and macerozyme, followed by rotary culture for 2 hours. Then, the culture medium was filtered through a nylon mesh (53 μm) and mixed with the same amount of W5 solution (154 mM NaCl, 125 mM $CaCl_2$, 5 mM KCl, 2 mM MES, pH 5.7). The mixture was centrifuged at 100×g to precipitate the protoplasts which were then added to MMg solution (0.4 M mannitol, 15 mM $MgCl_2$, 4 mM MES, pH 5.7).

In order to introduce the HvRAF gene into the protoplasts, a recombinant vector comprising a fusion of the HvRAF gene and a soluble modified green fluorescence protein (smgfp) reporter gene was prepared. For this purpose, the cDNA (SEQ ID NO: 3) of the HvRAF gene prepared in Example 1 as a template was subjected to PCR amplification using the following primers containing a restriction enzyme BamHI site.

```
Sense primer HvAP2-gfp-F3 (Bam)
5'-GGATCCAATGTGTGGCGGCGCCATCCTA-3'    (SEQ ID NO: 25)

Antisense primer HvAP2-gfp-R3 (Bam)
5'-GGATCCGCGAAGATGCTGTCGGCGGATTC-3'   (SEQ ID NO: 26)
```

The PCR amplification conditions were as follows: denaturation at 94° C. for 3 min; and then 5 cycles at 94° C. for 30 sec, 55° C. for 30 sec, and 72° C. for 1 min, followed by 30 cycles at 94° C. for 30 sec, 58° C. for 30 sec, and 72° C. for 1 min. The PCR amplification product was loaded on 1% agarose gel, and then a band at the position of about 1 kb was cut out with a knife and separated using the Accuprep gel extraction kit (Bioneer, Korea), followed by cloning into a pGEM T-easy vector (Promega). The recombinant vector was transformed into *E. coli* (DH10B), and the plasmid was isolated. The plasmid was treated with restriction enzyme BamHI, and the resulting fragment was cloned into a smgfp vector, thus preparing a recombinant vector comprising the HvRAF gene and the reporter gene.

20 μg of the recombinant vector was carefully mixed with 200 μl, of the above-isolated protoplasts, to which 220 μl of PEG/Ca 40% (v/v) solution (4 g of PEG4000; 3 ml of $H_2O$, 2.5 ml of 0.8 M mannitol, and 1 ml of 1 M $CaCl_2$) was added and mixed. Then, the mixture was centrifuged at 145×g for 1 minute to remove PEG. The resulting material was cultured in dark conditions for about one day, and then whether the HvRAF protein has migrated into the nuclei of the protoplasts was observed with a confocal microscope. At this time, a protoplast transformed with a smgfp vector comprising only the reporter gene without the HvRAF gene was used as a control group.

Figure 7:
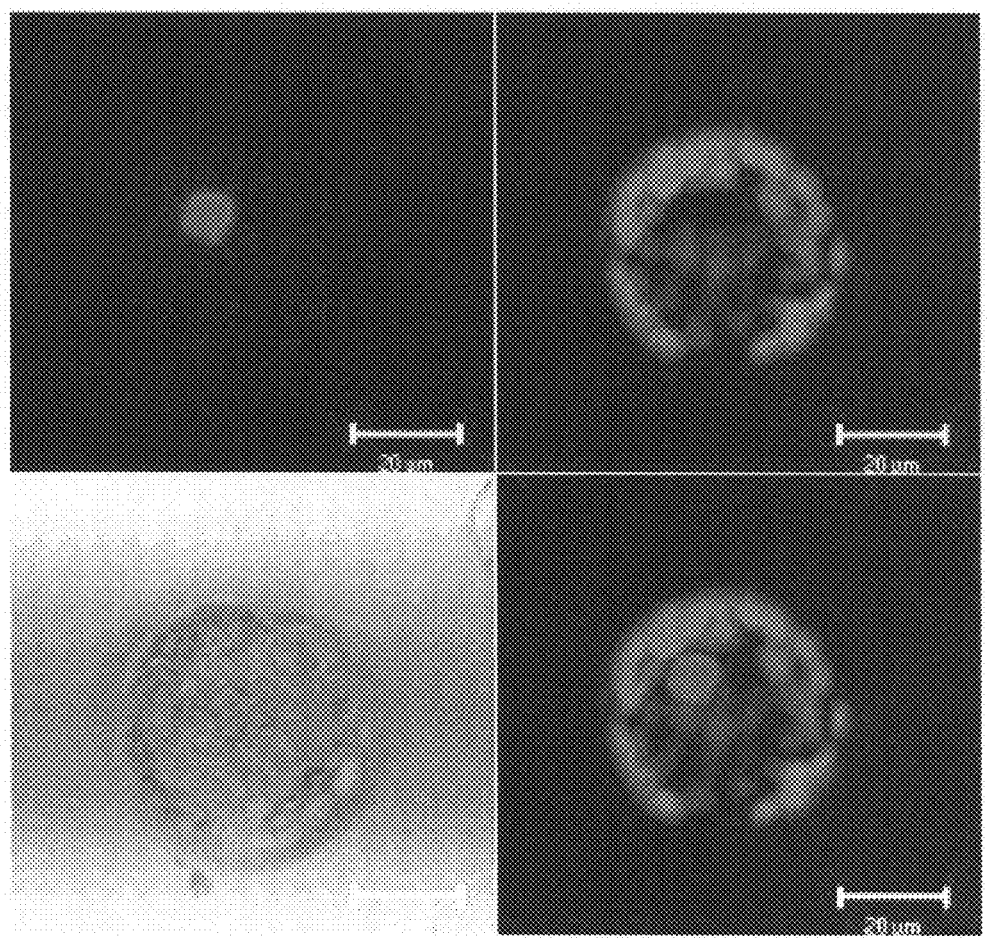
FIG. 7 shows the results of subcellular localization assay conducted by introducing into *Arabidopsis thaliana* protoplasts a vector comprising the inventive HvRAF gene and a reporter gene to examine whether the HvRAF protein migrates into the nucleus.
Figure 8:
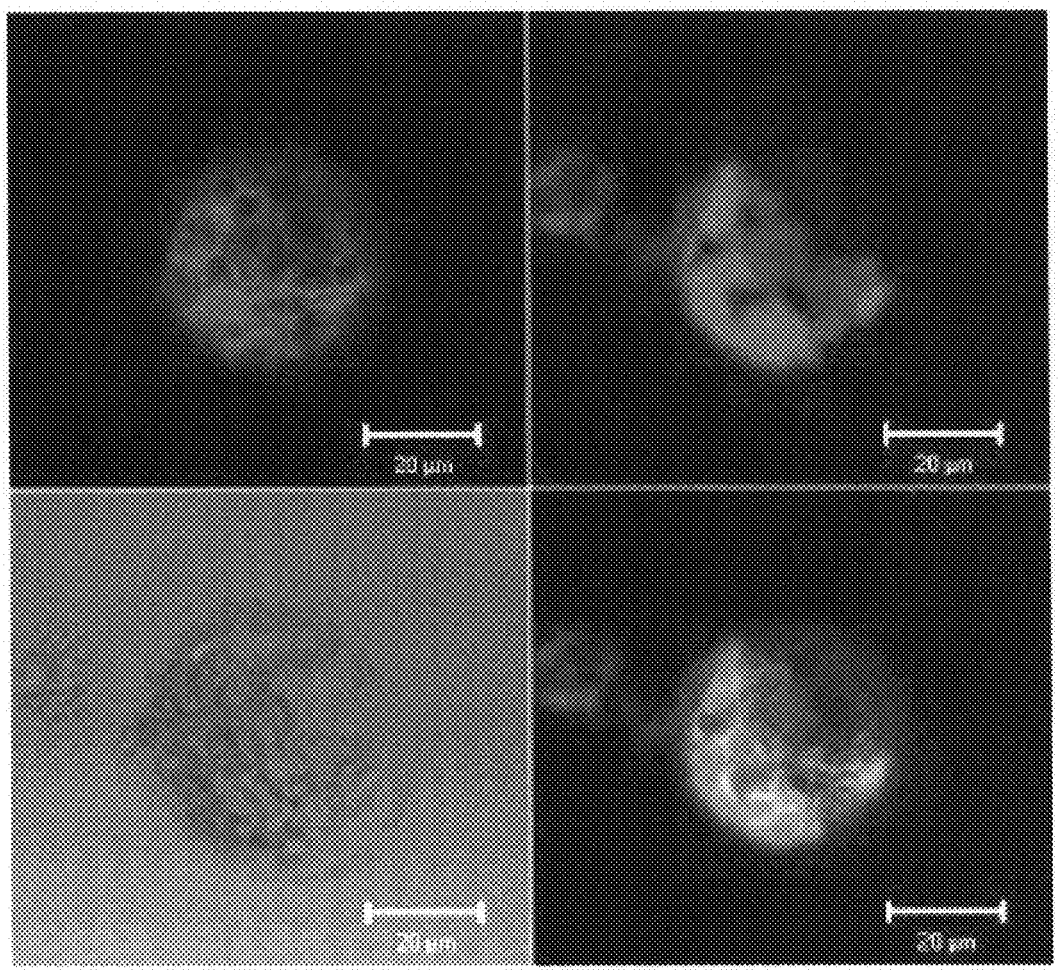
FIG. 8 shows the results of subcellular localization assay conducted by introducing into *Arabidopsis thaliana* protoplasts a vector comprising only a reporter gene without the inventive HvRAF gene to examine whether the HvRAF protein migrates into the nucleus.

From the test results, it could be found that, in the case of the protoplast transformed with the vector comprising the HvRAF gene and the reporter gene, the HvRAF::smgfp fusion protein migrated into the nucleus (see FIG. 7). On the other hand, in the case of the protoplast transformed with the vector comprising only the reporter gene without the HvRAF gene, it was observed that the smgfp protein spread throughout the cytoplasm including the nucleus (see FIG. 8).

Accordingly, it could be found that the HvRAF gene according to the present invention has the activity capable of migrating into the nucleus.

Example 6

Analysis of Transcription Activation Region of HvRAF Protein

In order to confirm whether the HvRAF protein actually activates the expression of a gene, a series of mutants of the HvRAF gene were constructed in a yeast system and analyzed for transcription activity.

For this purpose, a gene (SEQ ID NO: 3) encoding the entire HvRAF sequence (amino acids 1-328), gene fragments having sequential deletions in the N-terminus of the HvRAF gene (HvRAFΔN1: a gene fragment encoding amino acids 59-328; HvRAFΔN2: a gene fragment encoding amino acids 217-328: and HvRAFΔN3: a gene-fragment encoding amino acids 303-328), gene fragments having sequential deletions in the C-terminus of the HvRAF gene (HvRAFΔC1: a gene fragment encoding amino acids 1-316; HvRAFΔC2: a gene fragment encoding amino acids 1-294; and HvRAFΔC3: a gene fragment encoding amino acids 1-67), were prepared by PCR amplification using the following primers.

TABLE 2

Primers used in preparation of partial proteins for analysis of transcription activity of HvRAF protein

| Primers | Base sequences | SEQ ID NO |
| --- | --- | --- |
| HvAP2-acti-Full-F(EcoI) | 5'-GAATTCATGTGTGGCGGCGCCA TCCTAG-3' | 27 |
| HvAP2-acti-Full-R(PstI) | 5'-CTGCAGTCAGAAAATGGCGCTG TCC-3' | 28 |
| HvAP2-acti-C1(PstI) | 5'-CTGCAGCAGAGGCTGACGGCGT CCAT-3' | 29 |
| HvAP2-acti-C2(PstI) | 5'-CTGCAGGAAGATGCTGTCGGCG GATTC-3' | 30 |
| HvAP2-acti-C3(PstI) | 5'-CTGCAGGCAGGTCGAAGTGGTC ATCG-3' | 31 |
| HvAP2-acti-N1(EcoI) | 5'-GAATTCGAGGACTTCGATGACC ACTT-3' | 32 |

TABLE 2-continued

Primers used in preparation of partial proteins for analysis of transcription activity of HvRAF protein

| Primers | Base sequences | SEQ ID NO |
|---|---|---|
| HvAP2-acti-N2(EcoI) | 5'-GAATTCGAGCTGATGGAGTTTTT CAA-3' | 33 |
| HvAP2-acti-N3(EcoI) | 5'-GAATTCGCCCTCAGCGTGGACA GTG-3' | 34 |

Each of the above-prepared gene fragments was inserted into each of the EcoRI and PSt1 restriction enzyme cleavage sites of pGBKT7 (Clontech), a GAL4 DNA-binding vector, thus preparing recombinant vectors. Each of the recombinant vectors was transformed into yeast AH109 (Clontech). Transcription activity was determined by subjecting each of the transformed yeast strains to liquid culture while measuring β-galactosidase activity by colony lift filter assay using ONPG (o-nitrophenyl β-D-galactopyronosid) as a substrate. For a concrete test method, refer to the yeast protocol handbook (PT3024-1) of Clontech.

Figure 9:
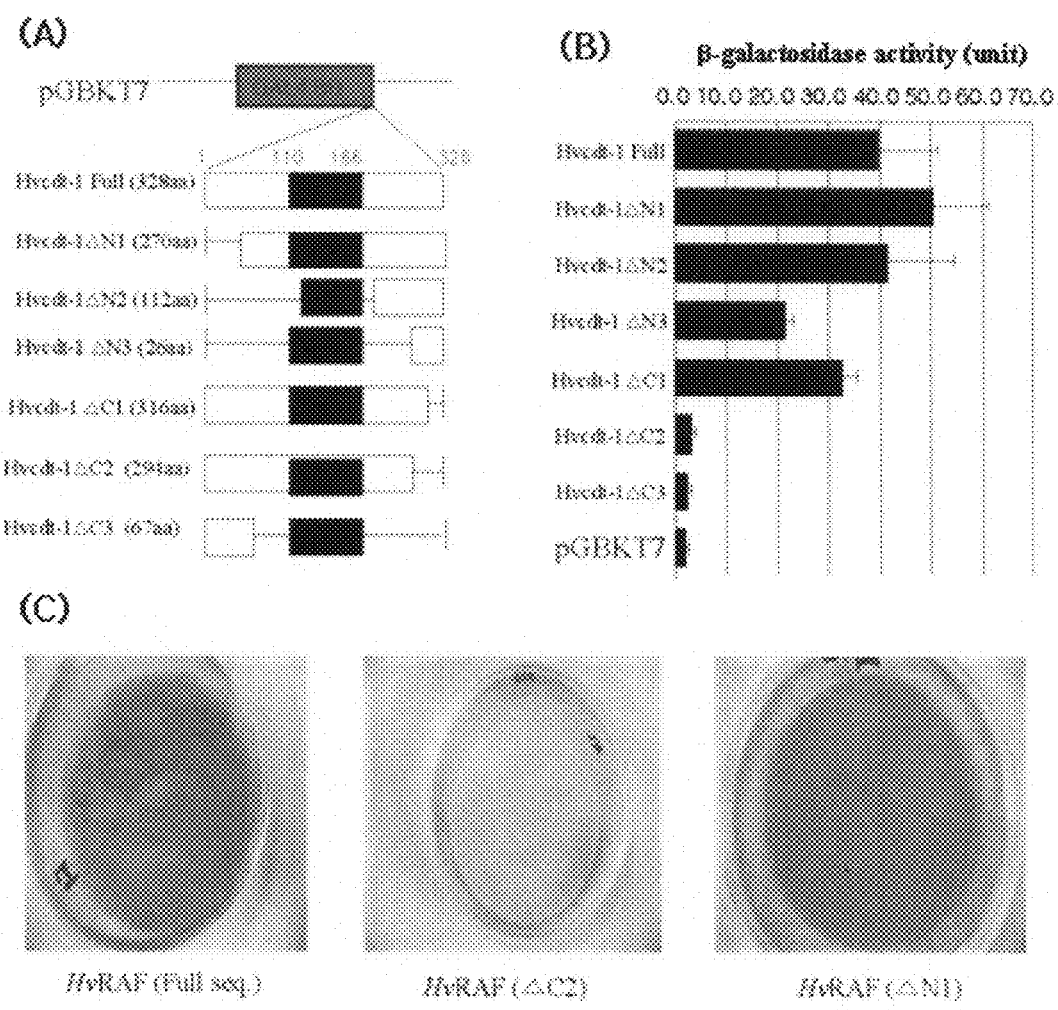
FIG. 9 shows the results of analysis of a transcription activation region, conducted by introducing a series of deletion mutants of the HvRAF gene (A) into GAL4 DNA-binding vectors, transforming the vectors into yeast and measuring the β-galactosidase activities of the deletion mutants by an assay using ONPG as a substrate (B) and a colony-lift filter assay (C).

The test results showed that the full-length HvRAF protein strongly induced the expression of β-galactosidase in a fusion with the GAL4 DNA-binding domain. This suggests that the HvRAF protein is a potent transcription control factor. Meanwhile, the gene fragments having deletions in the N-terminus has no great effect on transcription stimulation activity, but the gene fragment having a deletion of 34 amino acids in the C-terminus (HvRAFΔC2, amino acids 1-294) did not show β-galactosidase activity. On the other hand, the gene fragment having a deletion of 12 amino acids in the C-terminus (HvRAFΔC1, amino acids 1-316) maintained β-galactosidase activity. Thus, it could be found that amino acids 317-328 of the HvRAF protein has no connection with transcription activity. Meanwhile, the gene fragment encoding amino acids 303-328 (HvRAFΔN3) maintained β-galactosidase activity (see FIG. 9). From these test results, it could be found that 14 amino acids of amino acid residues 303-316 is a domain performing an important role in the transcription activity of the HvRAF protein. The amino acid sequence and base sequence of said 14 amino acids (Ala-Leu-Ser-Val-Asp-Ser-Gly-Met-Asp-Ala-Val-Ser-Leu-Trp) are set forth in SEQ ID NO: 35 and SEQ ID NO: 36, respectively.

Example 7

Induction of HvRAF Gene Expression by Various Environmental Stresses

In order to confirm the function of the HvRAF gene isolated in Example 1, whether the expression of the gene is induced by various environmental stresses was examined. The environmental stresses were induced by treatment with the following substances: plant hormones, such as salicylic acid, ethephon, methyl jasmonic acid and ABA(abscisic acid), which are known to be synthesized upon the penetration of pathogenic organisms into host plants and act to construct a defense system by various signaling pathways; cellulase, a cell wall digestive enzyme secreted upon wounding or the penetration of pathogenic microorganism into host plants; and methyl vilogen (MV; paraquat) known to induce active oxygen species in plants, leading to oxidative stress. Also, plants were treated with mechanical wounding.

More specifically, barley seedlings grown in vermiculite soil for 7 days were spread with each of 5 mM salicylic acid, 2 mM ethephon, 0.1 mM methyl jasmonic acid, and 0.1 mM ABA. After 1 hr, 3 hr, 6 hr and 18 hr, total RNA was extracted from the root of each of the seedlings in the same manner as in Example <4-1> and then subjected to Northern blot analysis.

Also, the roots of 14-day-old barley seedlings were treated with cellulase and MV at concentrations of 0.01% and 10 mM, respectively, and after 6 hours, total RNA was extracted from the leaf or root of each of the seedlings in the same manner as in Example <4-1> and then subjected to Northern blot analysis. At this time, a control group was treated with water in place of cellulase or MV.

Figure 10:
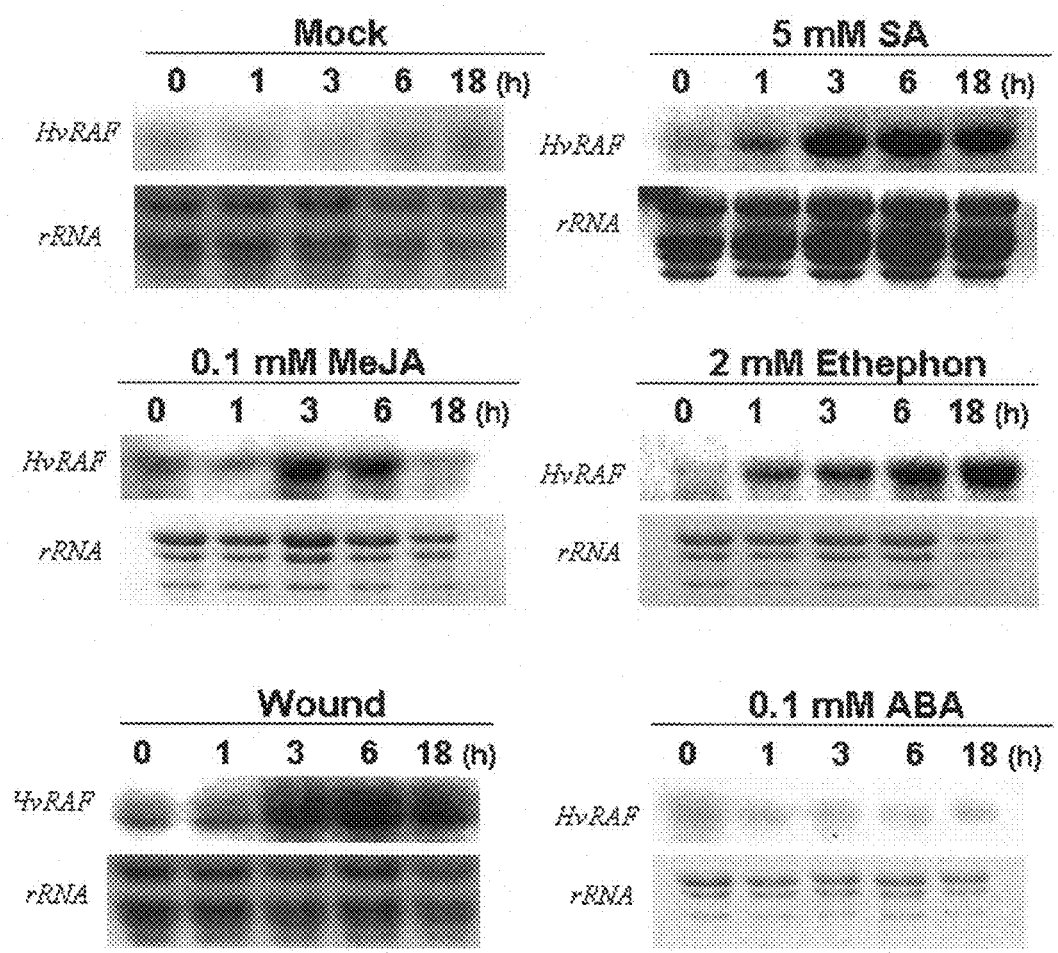
FIG. 10 shows the results of analysis for the expression patterns of the HvRAF genes in barley, caused by treatment with plant hormones, such as methyl jasmonic acid, ethephone and salicylic acid (Mock: control; Ethephon: treated with ethephone; SA: treated with salicylic acid; and MeJA: treated with methyl jasmonic acid).

From the test results, it could be observed that the expression of the inventive HvRAF gene was induced by plant hormones, such as salicylic acid, ethephon and methyl jasmonic acid as well as wounding. However, little induction was observed by either mock or ABA treatment (see FIG. 10).

Figure 11:
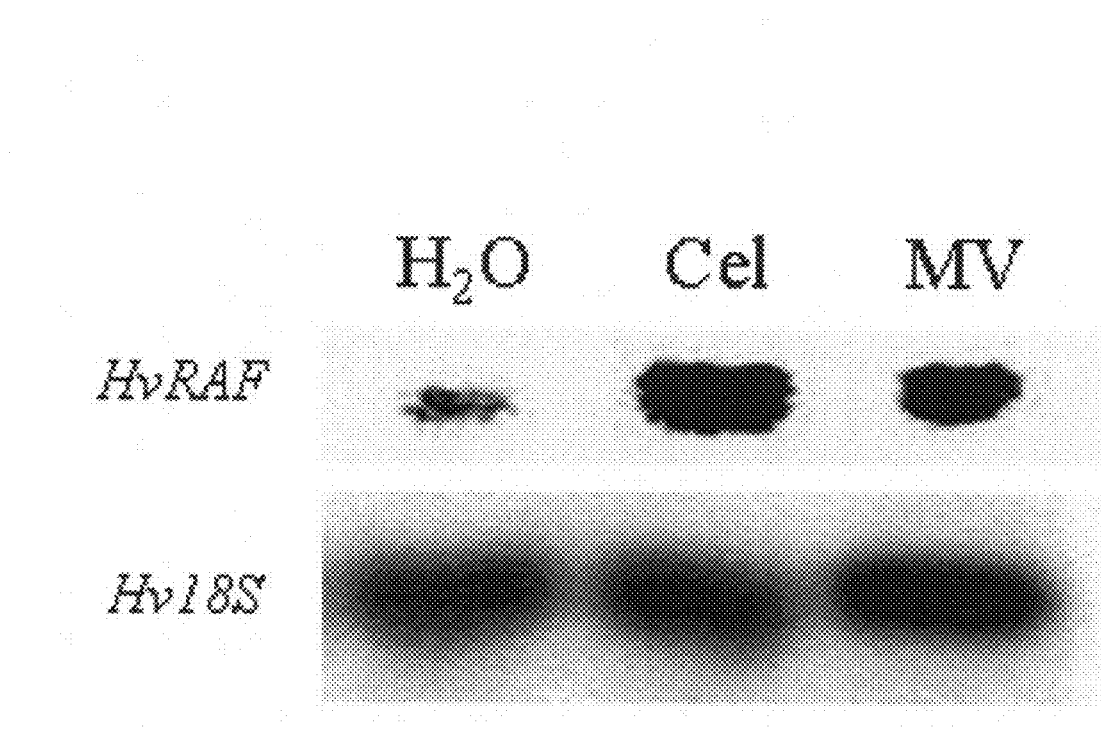
FIG. 11 shows the results of analysis for the expression patterns of the HvRAF gene in barley, caused by treatment with cellulase, water and methyl vilogen (MV; paraquat).

In addition, it could be observed that, in the case of treatment of the seedlings with cellulase or MV, the expression of the HvRAF gene was induced in the root (see FIG. 11).

From the above test results, it was inferred that, since the inventive HvRAF gene has a characteristic in that its expression is induced by various stresses, it would be associated with defense action against stresses in plants.

Example 8

Examination of Environmental Stress Resistance of HvRAF Gene-Overexpressed *Arabidopsis thaliana*

In order to confirm whether the inventive HvRAF gene is associated with the environmental stress resistance of plants, HvRAF gene-overexpressed *Arabidopsis thaliana* plants were produced and examined for resistance to environmental stresses, such as pathogen and high-concentration salt. Also, whether the overexpression of the HvRAF gene in *Arabidopsis thaliana* induces the expression of a pathogen resistance gene and a low-temperature-resistant gene was examined.

<8-1> Production of HvRAF Gene-Overexpressed *Arabidopsis thaliana*

The full-length cDNA (SEQ ID NO: 3) of the HvRAF gene prepared in Example 1 was inserted into the XabI and XhI restriction enzymes of plant binary vector pBI111L comprising a cabbage mosaic virus (CaMV) 35S promoter, thus preparing a recombinant vector. The recombinant vector was introduced into an *Agrobacterium* C58C1 strain by electroporation and then inoculated into YEP media (10 g yeast extract, 10 g peptone and 5 g NaCl per liter of medium) containing kanamycin, gentamycin and rifampicin at final concentrations of 30 µg/ml, 100 µg/ml and 100/ml, respectively, followed by culturing at 30° C. overnight. Then, a strain showing resistance to the antibiotics was selected, and transformed into wild-type *Arabidopsis thaliana* (Col-0) by the floral dip method. Namely, the selected *Agrobacterium* colony was inoculated into 5 ml of a YEP liquid medium containing the same concentration of antibiotics and cultured for one day, and 500 μl of the culture medium was inoculated into 500 ml of YEP medium and cultured to an absorbance of at least 2.0 at 600 nm. The culture medium was transferred into a tube and centrifuged at 4° C. at 5000 rpm, and the precipitate was suspended in infiltration buffer (2.2 g MS salt, 50 g sucrose, 0.5 g MES, 0.044 M benzylaminopurin and 200 μl Silwet L-77 per liter of buffer, pH 5.7). A wild-type *Arabidopsis thaliana* plant where the flower stalk has been about 5-10 cm tall was soaked three times in the suspension for 5-7 seconds each time. 3-4 weeks after the inoculation, the seeds were harvested and sowed in kanamyein-containing medium, and transgenic plants showing resistance were selected. RNA was extracted from the selected plants and subjected to Northern blot analysis in the same manner as in Example <4-1>.

Figure 12:
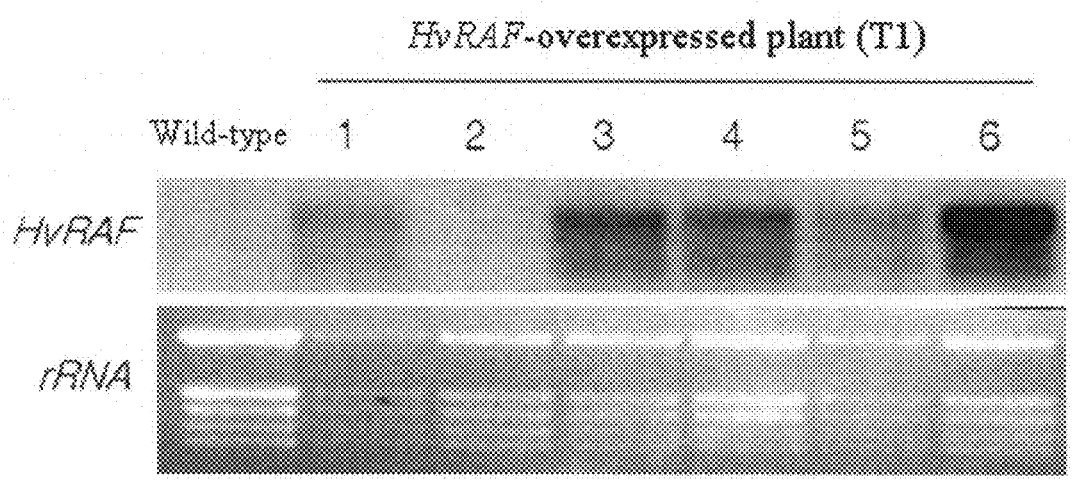
FIG. 12 shows the results of Northern blot analysis to select HvRAF gene-overexpressed transgenic plants. rRNA was used as a control.

As a result, two transgenic plants overexpressing the HvRAF gene (HvRAF-overexpressed plant #4, 35S::HvRAF4; and HvRAF-overexpressed plant #6, 35S::HvRAF6) was selected (FIG. 12).

<8-2> Examination of Pathogen Resistance of HvRAF Gene-Overexpressed Transgenic Plants The transformed *Arabidopsis thaliana* plants obtained in Example <8-1> were grown in soil for about 4 weeks, and then the root tips were cut about 2 cm.

The plants were immersed in 10 mM $MgCl_2$ containing about 108 cfu of *Ralstonia solannearum* GMI 1000 suspended therein for 2 hours, and transferred and grown in soil at 23° C. As a control group, wild-type *Arabidopsis thaliana* was used. From 2 days after inoculation with the pathogenic bacteria, the conditions of symptoms were examined by the disease index method. In the method, infection was rated on a scale of 0-4 according to the degree of soft rot symptoms in whole leaves. Namely, 0: whole leaves did not show soft rot symptoms; 1: 25% or less of whole leaves showed soft rot symptoms; 2: 26-50% showed soft rot symptoms; 3: 51-75% showed soft rot symptoms; and 4: 76-100% showed soft rot symptoms. Each test was repeated three times.

Figure 13:
FIG. 13 is a photograph of HvRAF gene-overexpressed *Arabidopsis thaliana* grown for 6 days after inoculation with *Ralstonia solanacearum*.
Figure 14:
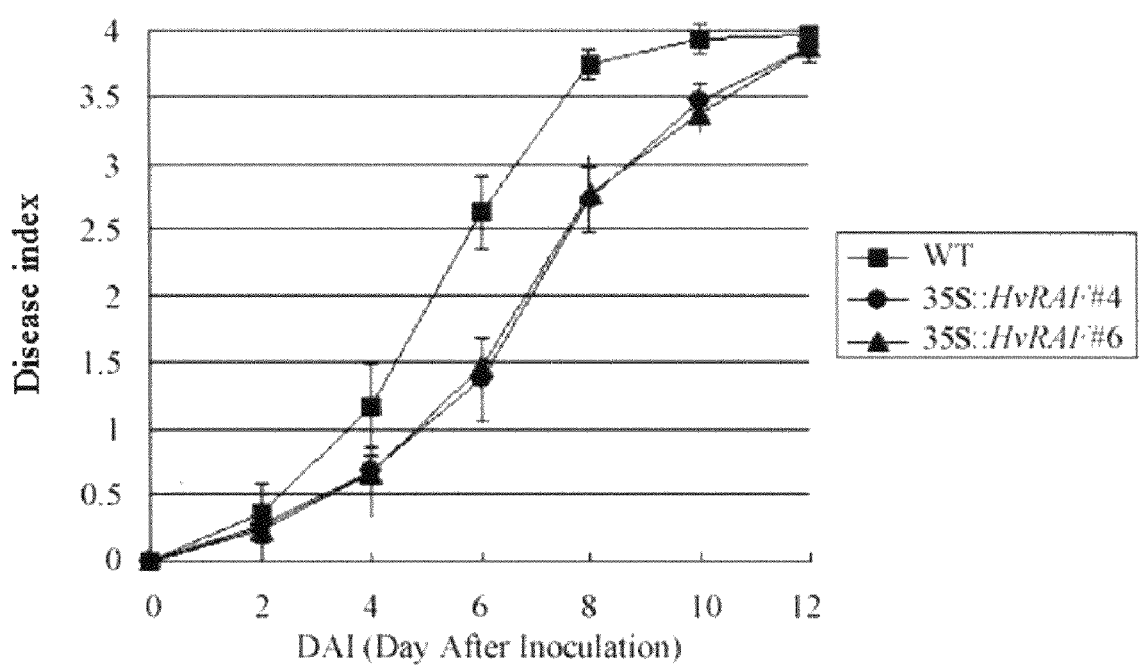
FIG. 14 is a graphic diagram showing the disease index of HvRAF gene-overexpressed *Arabidopsis thaliana* plants inoculated with *Ralstonia solanacearum*, with the passage of time (WT: wild-type *Arabidopsis thaliana*).

In the test results, at 6 days after inoculation with the *Ralstonia solanacearum* pathogenic bacteria, the wild-type *Arabidopsis thaliana* plant showed symptoms in 60% or more (disease index 3), whereas the HvRAF-overexpreressed transgenic plants showed symptoms in about 30% (disease index 2), which is about half that of the wild-type plant. At 8 days after inoculation with the pathogenic bacteria, the wild-type plant showed symptoms in 90% or more (disease index 4), and the transgenic plants showed symptoms in about 60% (disease index 3) (see FIGS. 13 and 14).

Thus, it could be found that the symptom rate of the HvRAF-overexpressed transgenic plants is slower than that of the wild-type plant. This suggests that the HvRAF gene isolated from barley, a monocotyledon, can perform defense mechanisms against pathogenic bacteria even in *Arabidopsis thaliana*, a dicotyledon.

<8-3> Examination of High-Concentration Salt Resistance of HvRAF Gene-Overexpressed Transgenic Plants The transformed *Arabidopsis thaliaria* plants obtained in Example <8-1> were inoculated in MS media containing 50 mM or 100 mM NaCl and cultured for 14 days, and then measured for growth degree and root length. At this time, wild-type *Arabidopsis thaliana* was used as a control.

Figure 15:
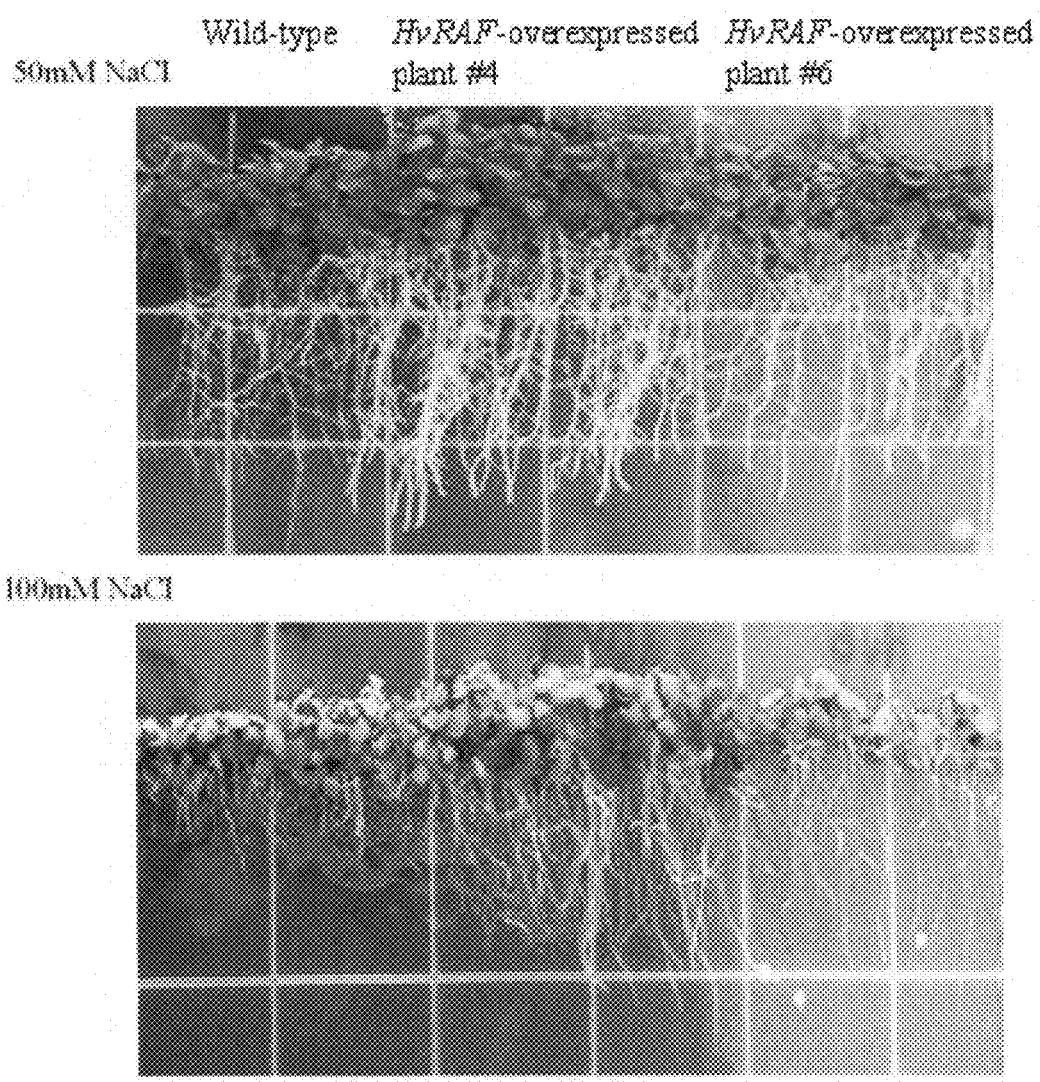
FIG. 15 is a photograph of HvRAF gene-overexpressed *Arabidopsis thaliana* cultured in a medium containing 50 mM or 100 mM NaCl for 14 days.
Figure 16:
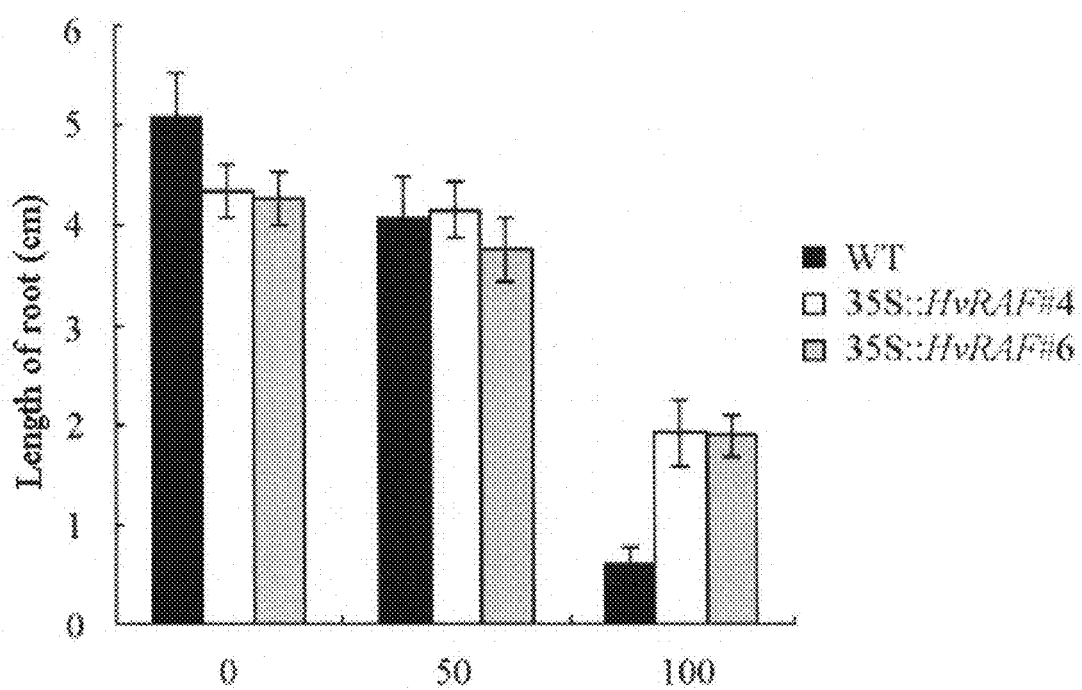
FIG. 16 is a graphic diagram showing measurement results for the root lengths of HvRAF gene-overexpressed *Arabidopsis thaliana* cultured in a medium containing 50 mM or 100 mM NaCl for 14 days. (WT: wild-type *Arabidopsis thaliana*).

In the test results, in the case of the medium containing 50 mM NaCl, there was no great difference in the degree of growth and root length between the wild-type plant and the transgenic plants, but in the case of the medium containing 100 mM NaCl, the growth degree and root length of the transgenic plants were at least two times longer than those of the wild-type plant (see FIGS. 15 and 16).

Thus, it could be found that, in an environment of high-concentration salt, the growth of the HvRAF-overexpressed transgenic plants is stronger than that of the wild-type plant. This suggests that the HvRAF gene isolated from barley, a monocotyledon, performs defense mechanisms against high-concentration salt stress even in *Arabidopsis thaliana*, a dicotyledon.

<8-4> Induction of Expression of Pathogen Resistance Genes and Low-Temperature Resistance Genes in HvRAF Gene-Overexpressed *Arabidopsis thaliana*

Whether the expression of pathogen resistance genes (biotic stress resistance gene) and low-temperature resistance genes (abiotic stress resistance gene) in HvRAF gene-overexpressed *Arabidopsis thaliana* was examined.

For this purpose, two lines (4-2, 4-8, 6-4, 6-6) of T3 generation of each of the transgenic plants ($T_1$) obtained in Example <8-1> were sowed in MS media and grown in a non-stress environment for 2 weeks. Then, the expression of pathogen resistance genes PDF1.2, PR1 and PR5, and low-temperature-resistant genes COR6.6 and GSH1, has been induced was examined by Northern blot analysis. As a control, wild-type *Arabidopsis thaliana* was used.

The Northern blot analysis was performed in the same manner as in Example <4-1>, except that RNAs isolated from the transgenic plants and the wild-type plants were used to prepare probes for pathogen resistance genes and low-temperature-resistant genes. Namely, the probes used in the Northern blot analysis were prepared by performing PCR amplification using the known sequence of each of the pathogen resistance genes and the low-temperature-resistant genes as a template with primers shown in Table 3 below.

TABLE 3

Primers used in preparation of probes for Northern blot analysis

| Probes | | Base sequences | SEQ ID NO |
|---|---|---|---|
| PDFL.2 (AY133787) | Sense | 5'-ATGGCTAAGTTTGCTTCCATC-3' | 37 |
| | Antisense | 5'-AATACACACCATTTAGCACCA-3' | 38 |
| PR1 (AY117187) | Sense | 5'-ATGAATTTTACTGGCTATTCT-3' | 39 |
| | Antisense | 5'-GTATGGCTTCTCGTTCACATA-3' | 40 |
| AtRP5 (ATU83490) | Sense | 5'-CCAGTATTCACATTCTCTTCTTCGT-3' | 41 |
| | Antisense | 5'-GTGGTTTTATCCCCATCTTTACATT-3' | 42 |
| COR6.6 (X62281) | Sense | 5'-TGAGAGGAGAAGAGCAATGT-3' | 43 |
| | Antisense | 5'-TGTCCTTCACGAAGTTAACAC-3' | 44 |

TABLE 3-continued

Primers used in preparation of probes for Northern blot analysis

| Probes | | Base sequences | SEQ ID NO |
|---|---|---|---|
| GSH1(AF068299) | Sense | 5'-GAATGGGAAAAAGTAATGGAAGGTG-3' | 45 |
| | Antisense | 5'-CTCTGGGAATATTGTTGTCAGATGG-3' | 46 |

Figure 17:
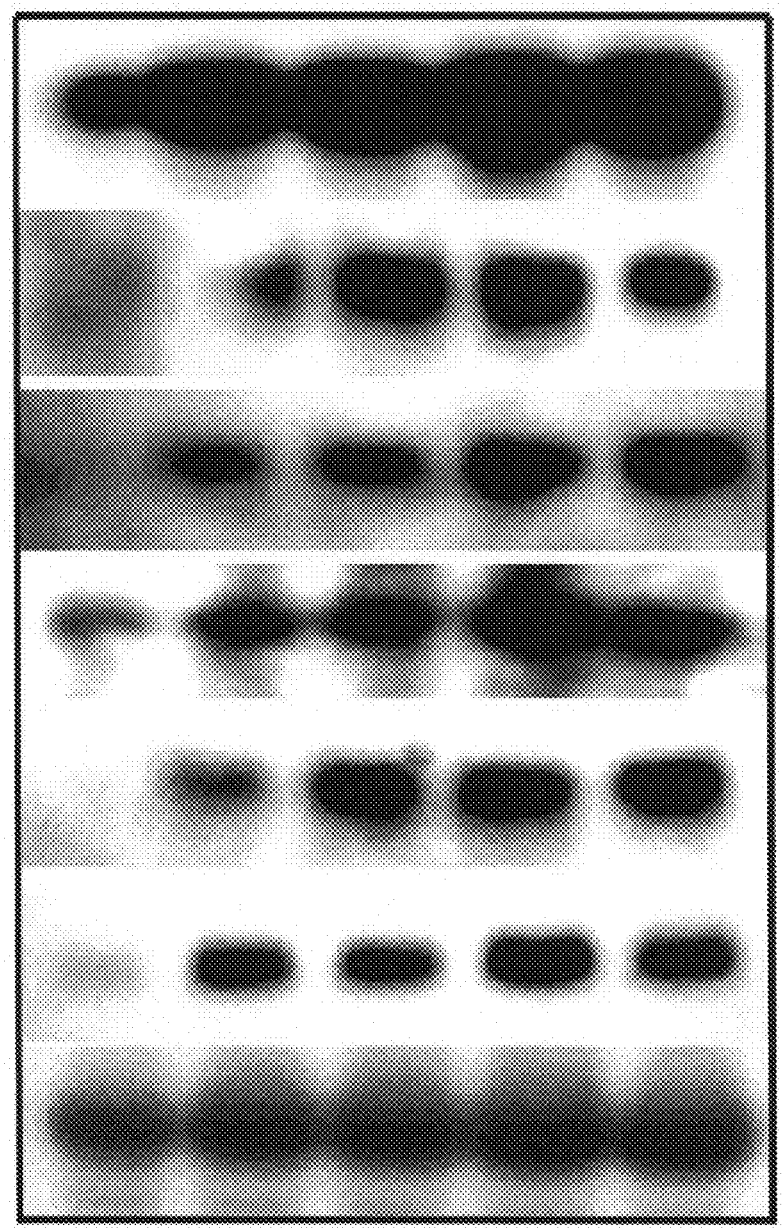
FIG. 17 shows the results of Northern blot analysis to examine whether the expressions of pathogen resistance genes and low-temperature-resistant genes in HvRAF gene-overexpressed *Arabidopsis thaliana* are induced (WT: wild-type *Arabidopsis thaliana*).

From the test results, it could be found that, in the case of the HvRAF gene-overexpressed *Arabidopsis thaliana*, the expression of not only the pathogen resistance genes PDF1.2, PR1 and PR5 but also the low-temperature-resistant genes COR6.6 and GSH1 was induced at higher levels than the wild-type plant (see FIG. 17).

Example 9

Verification of Germinability of Seed Obtained from HvRAF Gene-Overexpressed *Arabidopsis thaliana*

In order to confirm whether the seeds of the inventive HvRAF gene-overexpressed *Arabidopsis thaliana* have resistance to environmental stress, seeds were harvested from the HvRAF gene-overexpressed *Arabidopsis thaliana* produced in Example <8-1>. The harvested seeds were sowed in MS medium containing 1 μM plant hormone ABA (typical factor inhibiting germination) or high-concentration NaCl and measured for germinability. As a control, either seeds harvested from wild-type *Arabidopsis thaliana* or seeds harvested from *Arabidopsis thaliana* transformed with a vector not comprising HvRAF gene were sowed in the same condition and measured for germinability. To determine the germinability, the number of seeds where the radicle has penetrated out the testa by 1 mm or more was expressed as percentage.

Figure 18:
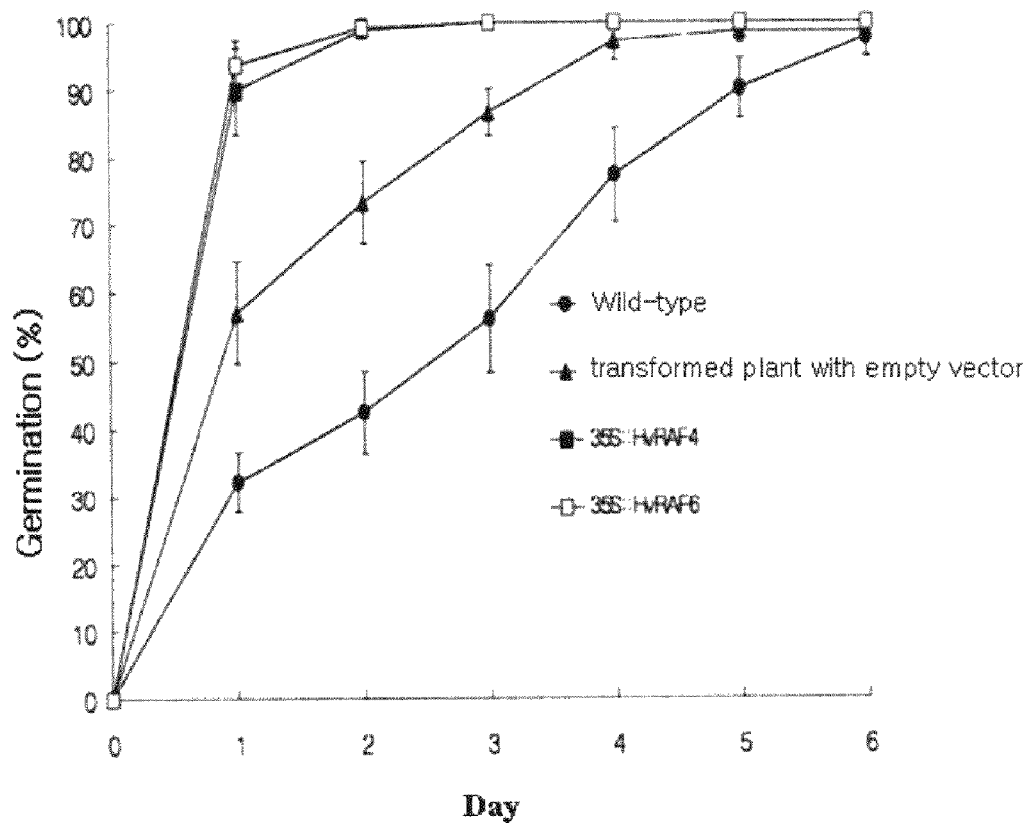
FIG. 18 shows measurement results for the germinability of seeds obtained from HvRAF gene-overexpressed *Arabidopsis thaliana* in a medium containing a high concentration of ABA.

In the test results, in the ABA-containing medium, the seeds of the HvRAF-overexpressed *Arabidopsis thaliana* plant had completely germinated only one day after sowing, whereas the seeds from the wild-type plant and the seeds from the *Arabidopsis thaliana* plant transformed with the vector not comprising HvRAF gene were completely germinated after 8 days and 4 days, respectively (see FIG. 18).

Figure 19:
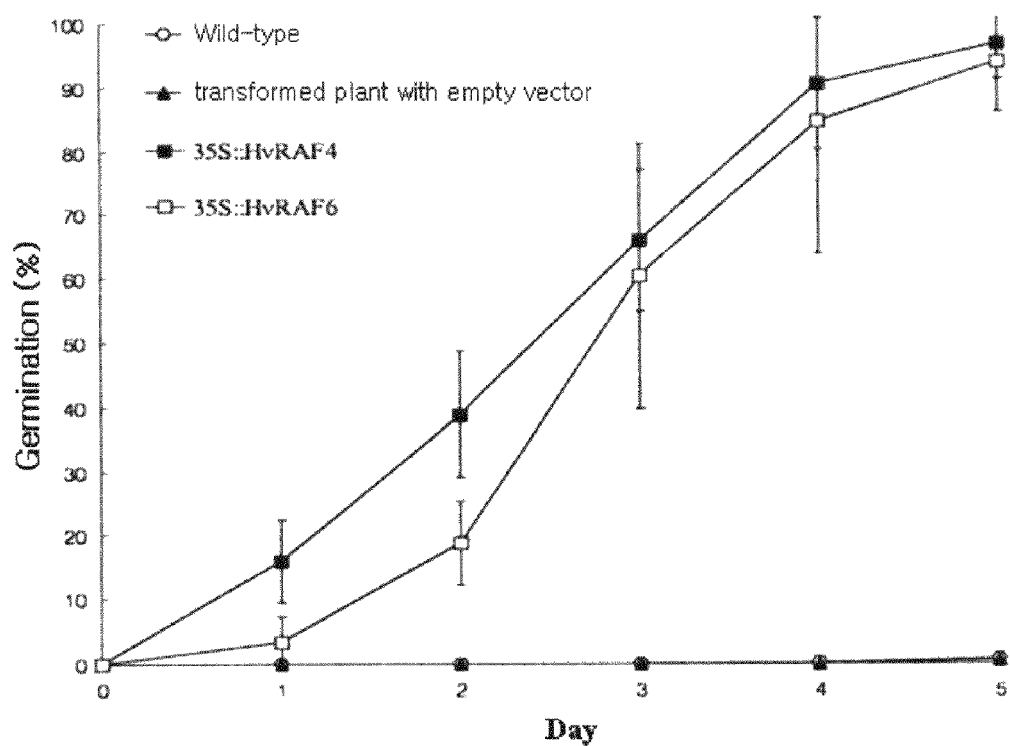
FIG. 19 shows measurement results for the germinability of seeds obtained from HvRAF gene-overexpressed *Arabidopsis thaliana* in a medium containing a high concentration of salt.

Also, in the case of sowing in media containing high-concentration salt, the HvRAF-overexpressed *Arabidopsis thaliana* seeds had completely germinated after 5 days, whereas the wild-type plant seeds and the empty vector-transformed *Arabidopsis thaliana* seeds were hardly geminated (see FIG. 19).

From the test results, it was found that the inventive HvRAF gene could also enhance the environmental stress resistance of seeds.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The entire disclosure of Korea Patent Application No. 2005-52321, filed on Jun. 17, 2005 including its specification, claims, drawings and summary are incorporated herein by reference in its entirety.

INDUSTRIAL APPLICABILITY

As described in the above embodiments, the inventive transcription factor has the effects of inducing the expression of genes associated with various environmental stresses, thus inhibiting or delaying a reduction in the growth or production of plants, caused by the environmental stresses.

The invention claimed is:

1. An isolated polypeptide having the amino acid sequence of SEQ ID NO: 4.

2. An isolated polynucleotide having the nucleotide sequence of SEQ ID NO: 3.

3. An isolated polynucleotide consisting of the nucleotide sequence of SEQ ID NO: 23.

4. A recombinant vector comprising the polynucleotide of claim 2.

5. A transformed bacterium with the recombinant vector of claim 4.

6. A method for enhancing the environmental stress resistance of a plant, comprising introducing the recombinant vector of claim 4 into the plant.

7. The method of claim 6, wherein the plant is monocotyledon or dicotyledon.

8. The method of claim 7, wherein the monocotyledon is selected from the group consisting of rice, wheat, barley, bamboo shoot, corn, taro, asparagus, onion, garlic, Welsh onion, leek, wild rocambole, yam and ginger.

9. The method of claim 7, wherein the dicotyledon is selected from the group consisting of *Arabidopsis thaliana*, eggplant, tobacco plant, red pepper, tomato, burdock, crown daisy, lettuce, balloon flower, spinach, chard, sweet potato, celery, carrot, water dropwort, parsley, Chinese cabbage, cabbage, radish, watermelon, melon, cucumber, pumpkin, gourd, strawberry, soybean, mung bean, kidney bean and pea.

10. The method of claim 6, wherein the environmental stress is selected from the group consisting of pathogenic microorganism, drought, low temperature and high-concentration of salt.

11. A recombinant vector comprising the polynucleotide of claim 3.

12. A transformed bacterium with the recombinant vector of claim 11.

13. A method for enhancing the environment stress resistance of a plant, comprising introducing the recombinant vector of claim 12 into the plant.

* * * * *

SEQUENCE LISTING

```
<160> NUMBER OF SEQ ID NOS: 47

<210> SEQ ID NO 1
<211> LENGTH: 21
<212> TYPE: DNA
<213> ORGANISM: Artificial Sequence
<220> FEATURE:
<223> OTHER INFORMATION: sense primer HvAP2-F

<400> SEQUENCE: 1
caggaagata aaacaatgtg t                                           21

<210> SEQ ID NO 2
<211> LENGTH: 21
<212> TYPE: DNA
<213> ORGANISM: Artificial Sequence
<220> FEATURE:
<223> OTHER INFORMATION: antisense primer HvAP2-R

<400> SEQUENCE: 2
gatcaattcg taggactatt g                                           21

<210> SEQ ID NO 3
```

```
<211> LENGTH: 987
<212> TYPE: DNA
<213> ORGANISM: Hordeum vulgare
<220> FEATURE:
<221> NAME/KEY: CDS
<222> LOCATION: (1)..(984)
<223> OTHER INFORMATION: HvRAF cDNA

<400> SEQUENCE: 3 atg tgt ggc ggc gcc atc cta gcg cag ctg atc ccg ccg tcg gcg ggc      48
Met Cys Gly Gly Ala Ile Leu Ala Gln Leu Ile Pro Pro Ser Ala Gly
 1               5                  10                  15 cgt ccg tcg aag cag gcg gca gcg ggc ggc cgg gcc ccg ccc acg agc      96
Arg Pro Ser Lys Gln Ala Ala Ala Gly Gly Arg Ala Pro Pro Thr Ser
             20                  25                  30 tcc aag aag ggc ggc gtg agc aag agc cgc cac agc agc acc cca gat     144
Ser Lys Lys Gly Gly Val Ser Lys Ser Arg His Ser Ser Thr Pro Asp
         35                  40                  45 gcc gac gac gac gtc ttc gag gcc gcc ttc gag gac ttc gat gac cac     192
Ala Asp Asp Asp Val Phe Glu Ala Ala Phe Glu Asp Phe Asp Asp His
     50                  55                  60 ttc gac ctg cgg gcg gag gag gac ggc ggc gac gac cat gtc gtc ttt     240
Phe Asp Leu Arg Ala Glu Glu Asp Gly Gly Asp Asp His Val Val Phe
 65                  70                  75                  80 gca tcc aag cct gcc ttc tct cca cgt ccg gcc tac gac ggt ggc cgc     288
Ala Ser Lys Pro Ala Phe Ser Pro Arg Pro Ala Tyr Asp Gly Gly Arg
                 85                  90                  95 gcg gcg cat gcg gcg agc agg aag aag cgc acc ggc cac ctc cat ggc     336
Ala Ala His Ala Ala Ser Arg Lys Lys Arg Thr Gly His Leu His Gly
            100                 105                 110 atc cgg cag cgg ccg tgg ggc aag tgg gcg gcg gag atc cgc gac ccg     384
Ile Arg Gln Arg Pro Trp Gly Lys Trp Ala Ala Glu Ile Arg Asp Pro
        115                 120                 125 cac aag ggc acc cgc gtc tgg ctc ggc acg ttc gac acg gcc gat gat     432
His Lys Gly Thr Arg Val Trp Leu Gly Thr Phe Asp Thr Ala Asp Asp
    130                 135                 140 gcc gcc cgg gcc tac gac gtc gcc gcc cgt cgc ctc cgt ggc agc aag     480
Ala Ala Arg Ala Tyr Asp Val Ala Ala Arg Arg Leu Arg Gly Ser Lys
145                 150                 155                 160 gcc aag gtc aac ttc ccc gac gcg gcc agg acc ggg gct cgc ccg cgc     528
Ala Lys Val Asn Phe Pro Asp Ala Ala Arg Thr Gly Ala Arg Pro Arg
                165                 170                 175 cgc gcc agc cgt aga acc gcg cag aaa ccg caa tgc ccc cct gcg cgg     576
Arg Ala Ser Arg Arg Thr Ala Gln Lys Pro Gln Cys Pro Pro Ala Arg
            180                 185                 190 acg acg gcg tac tct gcc acc gca gca gca cgc gca cag ccg gag cag     624
Thr Thr Ala Tyr Ser Ala Thr Ala Ala Ala Arg Ala Gln Pro Glu Gln
        195                 200                 205 gac gct atg atg gtc aaa ccc gag ctg atg gag ttt ttc aac gtg gac     672
Asp Ala Met Met Val Lys Pro Glu Leu Met Glu Phe Phe Asn Val Asp
    210                 215                 220 gcc atc gtc cac ctg acc act gcc gtc gcc gcg cta ccg cct gtc acg     720
Ala Ile Val His Leu Thr Thr Ala Val Ala Ala Leu Pro Pro Val Thr
225                 230                 235                 240 gcg agc acc ttc gcc gac acg atg ccg agg gtc gac gag gac tct tct     768
Ala Ser Thr Phe Ala Asp Thr Met Pro Arg Val Asp Glu Asp Ser Ser
                245                 250                 255 gtg ggg agc ggc ggc ggc gcc atg ctg ggg ttc gcc gac gag ctt ggg     816
Val Gly Ser Gly Gly Gly Ala Met Leu Gly Phe Ala Asp Glu Leu Gly
            260                 265                 270 ttc gat ccg ttc atg atg ttc cag cta ccc tgc tcg gac atg tac gaa     864
Phe Asp Pro Phe Met Met Phe Gln Leu Pro Cys Ser Asp Met Tyr Glu
```

```
            275                 280                 285
tcc gcc gac agc atc ttc gcc gga gac gct gtc atc ccg gat gcc ctc    912
Ser Ala Asp Ser Ile Phe Ala Gly Asp Ala Val Ile Pro Asp Ala Leu
    290                 295                 300 agc gtg gac agt ggc atg gac gcc gtc agc ctc tgg agc ttc gac gag    960
Ser Val Asp Ser Gly Met Asp Ala Val Ser Leu Trp Ser Phe Asp Glu
305                 310                 315                 320 ttc ccc atg gac agc gcc att ttc     tga                            987
Phe Pro Met Asp Ser Ala Ile Phe
                325
```

<210> SEQ ID NO 4
<211> LENGTH: 328
<212> TYPE: PRT
<213> ORGANISM: Hordeum vulgare

<400> SEQUENCE: 4

```
Met Cys Gly Gly Ala Ile Leu Ala Gln Leu Ile Pro Pro Ser Ala Gly
 1               5                  10                  15

Arg Pro Ser Lys Gln Ala Ala Gly Gly Arg Ala Pro Pro Thr Ser
            20                  25                  30

Ser Lys Lys Gly Gly Val Ser Lys Ser Arg His Ser Ser Thr Pro Asp
        35                  40                  45

Ala Asp Asp Asp Val Phe Glu Ala Ala Phe Glu Asp Phe Asp His
    50                  55                  60

Phe Asp Leu Arg Ala Glu Glu Asp Gly Gly Asp Asp His Val Val Phe
65                  70                  75                  80

Ala Ser Lys Pro Ala Phe Ser Pro Arg Pro Ala Tyr Asp Gly Gly Arg
                85                  90                  95

Ala Ala His Ala Ala Ser Arg Lys Lys Arg Thr Gly His Leu His Gly
            100                 105                 110

Ile Arg Gln Arg Pro Trp Gly Lys Trp Ala Ala Glu Ile Arg Asp Pro
        115                 120                 125

His Lys Gly Thr Arg Val Trp Leu Gly Thr Phe Asp Thr Ala Asp Asp
    130                 135                 140

Ala Ala Arg Ala Tyr Asp Val Ala Ala Arg Arg Leu Arg Gly Ser Lys
145                 150                 155                 160

Ala Lys Val Asn Phe Pro Asp Ala Ala Arg Thr Gly Ala Arg Pro Arg
                165                 170                 175

Arg Ala Ser Arg Arg Thr Ala Gln Lys Pro Gln Cys Pro Pro Ala Arg
            180                 185                 190

Thr Thr Ala Tyr Ser Ala Thr Ala Ala Arg Ala Gln Pro Glu Gln
        195                 200                 205

Asp Ala Met Met Val Lys Pro Glu Leu Met Glu Phe Phe Asn Val Asp
    210                 215                 220

Ala Ile Val His Leu Thr Thr Val Ala Ala Leu Pro Pro Val Thr
225                 230                 235                 240

Ala Ser Thr Phe Ala Asp Thr Met Pro Arg Val Asp Glu Ser Ser
                245                 250                 255

Val Gly Ser Gly Gly Ala Met Leu Gly Phe Ala Asp Glu Leu Gly
            260                 265                 270

Phe Asp Pro Phe Met Met Phe Gln Leu Pro Cys Ser Asp Met Tyr Glu
        275                 280                 285

Ser Ala Asp Ser Ile Phe Ala Gly Asp Ala Val Ile Pro Asp Ala Leu
    290                 295                 300

Ser Val Asp Ser Gly Met Asp Ala Val Ser Leu Trp Ser Phe Asp Glu
```

```
                305                 310                 315                 320
Phe Pro Met Asp Ser Ala Ile Phe
                325
```

<210> SEQ ID NO 5
<211> LENGTH: 16
<212> TYPE: DNA
<213> ORGANISM: Artificial Sequence
<220> FEATURE:
<223> OTHER INFORMATION: sense primer HvAP2-F2

<400> SEQUENCE: 5
acacgatgcc gagggt                                                    16

<210> SEQ ID NO 6
<211> LENGTH: 17
<212> TYPE: DNA
<213> ORGANISM: Artificial Sequence
<220> FEATURE:
<223> OTHER INFORMATION: antisense primer HvAP2-R2

<400> SEQUENCE: 6
agtacagaga ggtaccg                                                   17

<210> SEQ ID NO 7
<211> LENGTH: 22
<212> TYPE: DNA
<213> ORGANISM: Artificial Sequence
<220> FEATURE:
<223> OTHER INFORMATION: sense primer AP1

<400> SEQUENCE: 7
gtaatacgac tcactatagg gc                                             22

<210> SEQ ID NO 8
<211> LENGTH: 27
<212> TYPE: DNA
<213> ORGANISM: Artificial Sequence
<220> FEATURE:
<223> OTHER INFORMATION: antisense primer GSP1

<400> SEQUENCE: 8
tggagagaag gcaggcttgg atgcaaa                                        27

<210> SEQ ID NO 9
<211> LENGTH: 19
<212> TYPE: DNA
<213> ORGANISM: Artificial Sequence
<220> FEATURE:
<223> OTHER INFORMATION: sense primer AP2

<400> SEQUENCE: 9
actatagggc acgcgtggt                                                 19

<210> SEQ ID NO 10
<211> LENGTH: 27
<212> TYPE: DNA
<213> ORGANISM: Artificial Sequence
<220> FEATURE:
<223> OTHER INFORMATION: antisense primer GSP2

<400> SEQUENCE: 10
cccgcaggtc gaagtggtca tcgaagt                                        27

<210> SEQ ID NO 11
<211> LENGTH: 20

```
<212> TYPE: DNA
<213> ORGANISM: Artificial Sequence
<220> FEATURE:
<223> OTHER INFORMATION: sense primer T7

<400> SEQUENCE: 11
taatacgact cactataggg                                                    20

<210> SEQ ID NO 12
<211> LENGTH: 19
<212> TYPE: DNA
<213> ORGANISM: Artificial Sequence
<220> FEATURE:
<223> OTHER INFORMATION: antisense primer SP6

<400> SEQUENCE: 12
gatttaggtg acactatag                                                     19

<210> SEQ ID NO 13
<211> LENGTH: 26
<212> TYPE: DNA
<213> ORGANISM: Artificial Sequence
<220> FEATURE:
<223> OTHER INFORMATION: antisense primer GSP3

<400> SEQUENCE: 13
tacgtggcaa ggaggaacac acaatt                                             26

<210> SEQ ID NO 14
<211> LENGTH: 27
<212> TYPE: DNA
<213> ORGANISM: Artificial Sequence
<220> FEATURE:
<223> OTHER INFORMATION: antisense primer GSP4

<400> SEQUENCE: 14
acatgaactt gtcgcagcca cttggct                                            27

<210> SEQ ID NO 15
<211> LENGTH: 19
<212> TYPE: DNA
<213> ORGANISM: Artificial Sequence
<220> FEATURE:
<223> OTHER INFORMATION: primer Prom-1

<400> SEQUENCE: 15
cacattttgc acgacccgt                                                     19

<210> SEQ ID NO 16
<211> LENGTH: 20
<212> TYPE: DNA
<213> ORGANISM: Artificial Sequence
<220> FEATURE:
<223> OTHER INFORMATION: primer Prom-2

<400> SEQUENCE: 16
agtcgtccaa tgtaccggtt                                                    20

<210> SEQ ID NO 17
<211> LENGTH: 21
<212> TYPE: DNA
<213> ORGANISM: Artificial Sequence
<220> FEATURE:
<223> OTHER INFORMATION: primer Prom-3

<400> SEQUENCE: 17
ctacctgcac attgtagggc t                                                  21
```

-continued

<210> SEQ ID NO 18
<211> LENGTH: 22
<212> TYPE: DNA
<213> ORGANISM: Artificial Sequence
<220> FEATURE:
<223> OTHER INFORMATION: primer Prom-4

<400> SEQUENCE: 18
ccattacttg tgttaacctg ca                                        22

<210> SEQ ID NO 19
<211> LENGTH: 22
<212> TYPE: DNA
<213> ORGANISM: Artificial Sequence
<220> FEATURE:
<223> OTHER INFORMATION: primer Prom-5

<400> SEQUENCE: 19
ctcctacaac ttgatgattt gt                                        22

<210> SEQ ID NO 20
<211> LENGTH: 23
<212> TYPE: DNA
<213> ORGANISM: Artificial Sequence
<220> FEATURE:
<223> OTHER INFORMATION: primer Prom-6

<400> SEQUENCE: 20
cccttcgtta ataaacttga aca                                       23

<210> SEQ ID NO 21
<211> LENGTH: 19
<212> TYPE: DNA
<213> ORGANISM: Artificial Sequence
<220> FEATURE:
<223> OTHER INFORMATION: primer Prom-7

<400> SEQUENCE: 21
aactgcagtt gctggtgca                                            19

<210> SEQ ID NO 22
<211> LENGTH: 20
<212> TYPE: DNA
<213> ORGANISM: Artificial Sequence
<220> FEATURE:
<223> OTHER INFORMATION: primer Prom-8

<400> SEQUENCE: 22
aaccacacga cacacacgat                                           20

<210> SEQ ID NO 23
<211> LENGTH: 5658
<212> TYPE: DNA
<213> ORGANISM: Hordeum vulgare
<220> FEATURE:
<221> NAME/KEY: gene
<222> LOCATION: (1)..(5658)
<223> OTHER INFORMATION: HvRAF genomic DNA

<400> SEQUENCE: 23
cctgctcatg catcatttgt gttgttgcat cgtgtggtga atttcgtgta ttgatttgtg      60
tttccggttt gcttcgtctc gatagagttc cgcaagcgtg tcggattgtg tggacccgtt     120
cgactacgtc agttcgtcta cttcacggag gcattcttct tccaagcggg atctcaggca     180
agatgatcat ttccccagat accattacta taattgccat gctagtttta ccgcttctat     240

```
cgttatgtct cgttcctacc acatgttaaa tatcagcctc tcaacaatgc cttgaaacct    300
tcaacctgtt caacctagca aaccactgat tggctatgtt actgcttgct taaccctgtt    360
gatagcgttg ctagttgcag gtgcagatgc ttccatgtga atacatgtat tccttgttat    420
atcaccatat taaatgctat ttaatttaat gcaactatat acttggtaaa acgtggaagg    480
ctcggccttt ctagcctagt gttttgttcc acctttgccc ccttagtttc ggctaccggt    540
gttatgttcc ataaatgagc gctcctaaca cgatcggggt tgttatgggg accccttga    600 taattcgttt tagattaaag ctggtctggc aaggcccaac tttggtacta catttgccta    660
ataacctaat aataatgcat agggacccgc cggcacccgc ggactatttt aatcaacccc    720
cgggccagtg ctcctcatga gtgttggtcc cacctgagcg atgtccggca ccctctggt    780 cacccagagg tttagcgatc ccgacgtcta gctcatccgt catgtcctga aacgaggta    840 cgcgactcct atcgggatcg tcgacacatc gggcggcctt gctggattag ttttacctttt    900 gacgagatat cttgtgcatg gggattccgg tgatgctttg ggtaatctca gagttgaggt    960
tttccactag ggaatccgac gagatcgcga gcttcgtgat ggaggatttc tatgcggctt   1020
gtggtaattt gtgatggact agttggagca cccctgcagg gttaaatctt tcggaaagcc   1080
gtgcccgcgg ttatgtggca acgtggaaac tttgtttaac actggttaaa gataacttga   1140
agttaactta attaaaactt gccaactgtg tgcgtaaccg tgactgtctc cttcgtgagt   1200
tcttactccg atcgaggaca cggtggggtt atgtctgacg taggtaggtg ttcaggatca   1260
gtcatttgat catgagtagt tcacgtccgt tatgcataga tcttcccccct cttatttctt   1320 gtactcgtaa gttagccacc aaatatatgc ttagccgctg ttgcaacctc accacttaac   1380
catgcctcac ccattaagct tgctagtctt tgatacctt ggaaatgaga ttgttgagtc   1440
ccctgtggct cacagattac tacaacacca gttgcaggta caggtaaagg ttactcgacg   1500
tgagcgcgtt gattgttcat ttggagttgc ttcttcttct tcttcatcga tctaggatgg   1560
gttccaggcc gacagcctgg gatagcaagg atgaacgtcg ttcttctttt gtcgtttgtg   1620
ttcatccgta gtcggaccct ctcttactct tgatgaatat gtaatgtact gatgtgattc   1680
tgatgtggct tgtggcgagt gtaagccaac cctctattta tatctcttct tttcagtaca   1740
tgtacttgta acgatatcca ttcttgtgac acgacgagat gcgcttctaa ccctgacgag   1800
gccctcgtgc caaatggtta ggagagtggt tatagcccaa gccagtcgca tcccatattt   1860
aatgctctgt gtctcatttc tattgcttat aattttagtg ggcaacaata tcactaatgt   1920
ccctattagt ggtgaggtgt ctacaatgaa tatttccaat cctaaaagac tatgactctg   1980
gtgttcagtg cccattgtgt gtgtatgtga gtaaatggat tagctgatta atgtttgaca   2040
cattttatac acaaggtcaa tctacattgg atcaagaaaa tgttgagaaa gagtaaaacc   2100
caaggcttat gagtgttgtt gttgttgaag cacccccatgc atgattagag acaaggagaa   2160
agtgtgttat gaagaagatg attttttta aggagatgc atgcttagag aaattaaggt   2220
tagctagccg actaatccta ctaaaagtaa tacttgatta ttgtcgtttc aattaaaaaa   2280
ataccttgat tattgctgtt ccggttcgac gtcattggtc aagtaatcaa tcagtgatat   2340
caattaggtt aggcctaact aatacaagtg tcgtccatt tctttctggg tctaggctcg   2400
atcatttgcg gagctgagcc aagtggctcg cacaagttca tgtatcagga aaagttgag   2460 ctattcacgc gccaaattgt gtgttcctcc ttgccacgta gttgtgccgt gtcattcggc   2520
agctgactgt tgtgttcctg gcttcctgcc acctggcatc atgtgatgcc acctcagttg   2580
ttgagtcgtc caatgtaccg gttccctgtc aaccgagaaa atcggctatt tgccactttt   2640
```

```
aatattgggc ttctcaaaat tgccactctc aagattggtt tcgtaaaaat gtcatccaac    2700
ccatgtgtac tttgattaca atgccatttc ctcttttca atgctttcct ttttcttttc    2760
ccatttccca acatctgaag ggaccaatat accctagcc tatgcacatg tactagtttt    2820
ttgcatccaa cttgaaacaa cgccgttgag cgcccgccgt cggccgagat caccgcatac    2880
agttcgccaa gccctcctct ggtcctcccc catgatccat cagctcttct acctgcacat    2940
tgtagggctg ctcctgcttg ccgattgctt ggaagtgggc tgccgattgg ctggacatcg    3000
cgtgtcacag gttgcctgga cgccatgcgc ccacgcgcct cttatcgaca ctctgcgtca    3060
tctatctcta ggtatcgcag tggaatggaa ctcaatcctt ctacacagta ttcttctatc    3120
tgtaccttcg aatatgccat tacttgtgtt aacctgcaca tcagagacaa ctagtagaag    3180
tatacaaggg aaatttaga atatgtaaat tctattctgc atggttcatt tagaatgatg    3240
tcatgttctc ctacaacttg atgatttgtt ctaccttggt ggtgttatgt acatgtcatt    3300
gataccacat tacattcagg caaactgtag cgaatcttct gaatatatgt tcaacaatat    3360
gaaaatgaga agcaacgtgt tcatttcatt gtataacaca catacatgca gacgccttgc    3420
tttcttgttg ggagaggata catcttcaca agcaacaaca acaactacag aggatgtcca    3480
ctacagctcc aacaaagaag ttgactccaa aaagaaagct aaaaattgaa attggatgaa    3540
cgatctctac gaaattgatg ctatagttat ttgaggaagt tgaatactcc cttcgttaat    3600
aaacttgaac atctaggtta cctgcatgtt cctgcctcac ctctctagca tgtcacacga    3660
cgagctgcgc tagcgcacat gcacggatga gctgcggttg ctcgcgggca tggccggcaa    3720
gctatacgac ggctcgtgca aatgtggacg agcaccaacg gcgagctccg ccgtcgcgca    3780
caggcttggg tgagcaacgg tgggtggtgg cgaactgcag ttgctggtgc aggcgttggc    3840
aagctagggc ggcgagctgc gatgcctcgc actggcatca gcgagctacg gcgacgggct    3900
ttggtggaga acgaaacacc tcacagaccc aaccaatcca cacaggcgtg agataaggtt    3960
gaattatcca ggggtatttt ggtcccttca ggtgccagga aatggaaaaa gaaaagaaa    4020 accaataaaa aagagaaaat ggcatgttaa tcaaagtgca atcaaactga gtggcacttt    4080
tacgcagcca atcttaagag tggcaatttt gagaagccga gtattgaaaa tggtaaataa    4140
ccaattttct cctgccaacc acacgacaca cacgatcgtc ttggtcagct agcttgcgtt    4200
tataagtagg cgcagctccg tctctcggtg accaacacaa gacgtgagag aagaaagcgc    4260
gagacaggaa gataaaacaa tgtgtggcgg cgccatccta gcgcagctga tcccgccgtc    4320
ggcgggccgt ccgtcgaagc aggcggcagc gggcggccgg gccccgccca cgagctccaa    4380
gaagggcggc gtgagcaaga gccgccacag cagcaccca gatgccgacg acgacgtctt    4440
cgaggccgcc ttcgaggact tcgatgacca cttcgacctg cgggcggagg aggacggcgg    4500
cgacgaccat gtcgtctttg catccaagcc tgccttctct ccacgtccgg cctacgacgg    4560
tggccgcgcg gcgcatgcgg cgagcaggaa gaagcgcacc ggccacctcc atggcatccg    4620
gcagcggccg tggggcaagt gggcggcgga gatccgcgac ccgcacaagg gcacccgcgt    4680
ctggctcggc acgttcgaca cggccgatga tgccgcccgg gcctacgacg tcgccgcccg    4740
tcgcctccgt ggcagcaagg ccaaggtcaa cttccccgac gcggccagga ccggggctcg    4800
cccgcgccgc gccagccgta gaaccgcgca gaaaccgcaa tgcccccctg cgcggacgac    4860
ggcgtactct gccaccgcag cagcacgcgc acagccggag caggacgcta tgatggtcaa    4920
acccgagctg atggagtttt tcaacgtgga cgccatcgtc cacctgacca ctgccgtcgc    4980
cgcgctaccg cctgtcacgg cgagcacctt cgccgacacg atgccgaggg tcgacgagga    5040
```

-continued

```
ctcttctgtg gggagcggcg gcggcgccat gctggggttc gccgacgagc ttgggttcga    5100
tccgttcatg atgttccagc taccctgctc ggacatgtac gaatccgccg acagcatctt    5160
cgccggagac gctgtcatcc cggatgccct cagcgtggac agtggcatgg acgccgtcag    5220
cctctggagc ttcgacgagt tccccatgga cagcgccatt ttctgacgct tccgtgtga     5280
tgcactgcac tctgttggtt gtaagaatct ccacctggcc tctacgtagt tccttgtaaa    5340
tgcccgcgca cagaaccttg ctcagaccag attctgtttc ttggccagga acgaaggaa     5400
gggttgctgc cgatgcatga ttgcttcctc gatgaacgca gattcgaaat gtattctact    5460
gtttgagttt cttgttcgtc acacactgta ccaaactgta ttgtacccta tcataatttc    5520
tgctcggtac ctctctgtac tgctggtacc aaactgtatt gtactctgtc atgatctgta    5580
ctagtctttg gtactgctgg tcaatagtcc tacgaattga tcaaaaaaaa aaaaaaaaaa    5640
aaaaaaaaaa aaaaaaaa                                                  5658

<210> SEQ ID NO 24
<211> LENGTH: 4279
<212> TYPE: DNA
<213> ORGANISM: Hordeum vulgare
<220> FEATURE:
<221> NAME/KEY: promoter
<222> LOCATION: (1)..(4279)
<223> OTHER INFORMATION: HvRAF promoter

<400> SEQUENCE: 24
cctgctcatg catcatttgt gttgttgcat cgtgtggtga atttcgtgta ttgatttgtg      60
tttccggttt gcttcgtctc gatagagttc cgcaagcgtg tcggattgtg tggacccgtt     120
cgactacgtc agttcgtcta cttcacggag gcattcttct tccaagcggg atctcaggca     180
agatgatcat ttccccagat accattacta taattgccat gctagtttta ccgcttctat     240
cgttatgtct cgttcctacc acatgttaaa tatcagcctc tcaacaatgc cttgaaacct     300
tcaacctgtt caacctagca aaccactgat tggctatgtt actgcttgct taaccctgtt     360
gatagcgttg ctagttgcag gtgcagatgc ttccatgtga atacatgtat tccttgttat     420
atcaccatat taaatgctat ttaatttaat gcaactatat acttggtaaa acgtggaagg     480
ctcggccttt ctagcctagt gttttgttcc acctttgccc ccttagtttc ggctaccggt     540
gttatgttcc ataaatgagc gctcctaaca cgatcggggt tgttatgggg acccccttga     600
taattcgttt tagattaaag ctggtctggc aaggcccaac tttggtacta catttgccta     660
ataacctaat aataatgcat agggacccgc cggcacccgc ggactatttt aatcaacccc     720
cgggccagtg ctcctcatga gtgttggtcc cacctgagcg atgtccggca cccctctggt     780
cacccagagg tttagcgatc ccgacgtcta gctcatccgt catgtcctga aacgaggta      840
cgcgactcct atcgggatcg tcgacacatc gggcggcctt gctggattag tttttacctt     900
gacgagatat cttgtgcatg gggattccgg tgatgctttg ggtaatctca gagttgaggt     960
tttccactag gaatccgac  gagatcgcga gcttcgtgat ggaggatttc tatgcggctt    1020
gtggtaattt gtgatggact agttggagca ccctgcagg gttaaatctt tcggaaagcc     1080
gtgcccgcgg ttatgtggca acgtggaaac tttgtttaac actggttaaa gataacttga    1140
agttaactta attaaaactt gccaactgtg tgcgtaaccg tgactgtctc cttcgtgagt    1200
tcttactccg atcgaggaca cggtggggtt atgtctgacg taggtaggtg ttcaggatca    1260
gtcatttgat catgagtagt tcacgtccgt tatgcataga tcttcccct cttatttctt     1320
gtactcgtaa gttagccacc aaatatatgc ttagccgctg ttgcaacctc accacttaac    1380
```

```
catgcctcac ccattaagct tgctagtct tgatacccttt ggaaatgaga ttgttgagtc   1440
ccctgtggct cacagattac tacaacacca gttgcaggta caggtaaagg ttactcgacg   1500
tgagcgcgtt gattgttcat ttggagttgc ttcttcttct tcttcatcga tctaggatgg   1560
gttccaggcc gacagcctgg gatagcaagg atgaacgtcg ttcttctttt gtcgtttgtg   1620
ttcatccgta gtcggaccct ctcttactct tgatgaatat gtaatgtact gatgtgattc   1680
tgatgtggct tgtggcgagt gtaagccaac cctctatta tatctcttct tttcagtaca   1740
tgtacttgta acgatatcca ttcttgtgac acgacgagat gcgcttctaa ccctgacgag   1800
gccctcgtgc caaatggtta ggagagtggt tatagcccaa gccagtcgca tcccatattt   1860
aatgctctgt gtctcatttc tattgcttat aattttagtg ggcaacaata tcactaatgt   1920
ccctattagt ggtgaggtgt ctacaatgaa tatttccaat cctaaaagac tatgactctg   1980
gtgttcagtg cccattgtgt gtgtatgtga gtaaatggat tagctgatta atgtttgaca   2040
cattttatac acaaggtcaa tctacattgg atcaagaaaa tgttgagaaa gagtaaaacc   2100
caaggcttat gagtgttgtt gttgttgaag cacccatgc atgattagag acaaggagaa   2160
agtgtgttat gaagaagatg attttttta aggagatgc atgcttagag aaattaaggt   2220
tagctagccg actaatccta ctaaaagtaa tacttgatta ttgtcgtttc aattaaaaaa   2280
ataccttgat tattgctgtt ccggttcgac gtcattggtc aagtaatcaa tcagtgatat   2340
caattaggtt aggcctaact aatacaagtg gtcgtccatt tctttctggg tctaggctcg   2400
atcatttgcg gagctgagcc aagtggctcg cacaagttca tgtatcagga aaagttgag   2460 ctattcacgc gccaaattgt gtgttcctcc ttgccacgta gttgtgccgt gtcattcggc   2520
agctgactgt tgtgttcctg gcttcctgcc acctggcatc atgtgatgcc acctcagttg   2580
ttgagtcgtc caatgtaccg gttccctgtc aaccgagaaa atcggctatt gccactttt   2640 aatattgggc ttctcaaaat tgccactctc aagattggtt tcgtaaaaat gtcatccaac   2700
ccatgtgtac tttgattaca atgccatttc ctcttttca atgctttcct ttttctttc   2760 ccatttccca acatctgaag ggaccaatat accctagcc tatgcacatg tactagtttt   2820
ttgcatccaa cttgaaacaa cgccgttgag cgcccgccgt cggccgagat caccgcatac   2880
agttcgccaa gccctcctct ggtcctcccc catgatccat cagctcttct acctgcacat   2940
tgtagggctg ctcctgcttg ccgattgctt ggaagtgggc tgccgattgg ctggacatcg   3000
cgtgtcacag gttgcctgga cgccatgcgc ccacgcgcct cttatcgaca ctctgcgtca   3060
tctatctcta ggtatcgcag tggaatggaa ctcaatcctt ctacacagta ttcttctatc   3120 tgtacctttcg aatatgccat tacttgtgtt aacctgcaca tcagagacaa ctagtagaag   3180
tatacaaggg aaatttaga atatgtaaat tctattctgc atggttcatt tagaatgatg   3240
tcatgttctc ctacaacttg atgatttgtt ctaccttggt ggtgttatgt acatgtcatt   3300
gataccacat tacattcagg caaactgtag cgaatcttct gaatatatgt tcaacaatat   3360
gaaaatgaga agcaacgtgt tcatttcatt gtataacaca catacatgca gacgccttgc   3420
tttcttgttg ggagaggata catcttcaca agcaacaaca acaactacag aggatgtcca   3480
ctacagctcc aacaaagaag ttgactccaa aaagaaagct aaaaattgaa attggatgaa   3540
cgatctctac gaaattgatg ctatagttat ttgaggaagt tgaatactcc cttcgttaat   3600
aaacttgaac atctaggtta cctgcatgtt cctgcctcac ctctctagca tgtcacacga   3660
cgagctgcgc tagcgcacat gcacggatga gctgcggttg ctcgcgggca tggccggcaa   3720
gctatacgac ggctcgtgca aatgtggacg agcaccaacg gcgagctccg ccgtcgcgca   3780
```

-continued

```
caggcttggg tgagcaacgg tgggtggtgg cgaactgcag ttgctggtgc aggcgttggc   3840
aagctagggc ggcgagctgc gatgcctcgc actggcatca gcgagctacg gcgacgggct   3900
ttggtggaga acgaaacacc tcacagaccc aaccaatcca cacaggcgtg agataaggtt   3960
gaattatcca ggggtatttt ggtcccttca ggtgccagga aatggaaaaa gaaaagaaa    4020 accaataaaa aagagaaaat ggcatgttaa tcaaagtgca atcaaactga gtggcacttt   4080
tacgcagcca atcttaagag tggcaatttt gagaagccga gtattgaaaa tggtaaataa   4140
ccaattttct cctgccaacc acacgacaca cacgatcgtc ttggtcagct agcttgcgtt   4200
tataagtagg cgcagctccg tctctcggtg accaacacaa gacgtgagag aagaaagcgc   4260
gagacaggaa gataaaaca                                                4279
```

```
<210> SEQ ID NO 25
<211> LENGTH: 28
<212> TYPE: DNA
<213> ORGANISM: Artificial Sequence
<220> FEATURE:
<223> OTHER INFORMATION: sense primer HvAP2-gfp-F3(Bam)

<400> SEQUENCE: 25
ggatccaatg tgtggcggcg ccatccta                                      28

<210> SEQ ID NO 26
<211> LENGTH: 29
<212> TYPE: DNA
<213> ORGANISM: Artificial Sequence
<220> FEATURE:
<223> OTHER INFORMATION: antisense primer HvAP2-gfp-R3(Bam)

<400> SEQUENCE: 26
ggatccgcga agatgctgtc ggcggattc                                     29

<210> SEQ ID NO 27
<211> LENGTH: 28
<212> TYPE: DNA
<213> ORGANISM: Artificial Sequence
<220> FEATURE:
<223> OTHER INFORMATION: primer HvAP2-acti-Full-F

<400> SEQUENCE: 27
gaattcatgt gtggcggcgc catcctag                                      28

<210> SEQ ID NO 28
<211> LENGTH: 25
<212> TYPE: DNA
<213> ORGANISM: Artificial Sequence
<220> FEATURE:
<223> OTHER INFORMATION: primer HvAP2-acti-Full-R

<400> SEQUENCE: 28
ctgcagtcag aaaatggcgc tgtcc                                         25

<210> SEQ ID NO 29
<211> LENGTH: 26
<212> TYPE: DNA
<213> ORGANISM: Artificial Sequence
<220> FEATURE:
<223> OTHER INFORMATION: primer HvAP2-acti-C1

<400> SEQUENCE: 29
ctgcagcaga ggctgacggc gtccat                                        26
```

```
<210> SEQ ID NO 30
<211> LENGTH: 27
<212> TYPE: DNA
<213> ORGANISM: Artificial Sequence
<220> FEATURE:
<223> OTHER INFORMATION: primer HvAP2-acti-C2

<400> SEQUENCE: 30
ctgcaggaag atgctgtcgg cggattc                                        27

<210> SEQ ID NO 31
<211> LENGTH: 26
<212> TYPE: DNA
<213> ORGANISM: Artificial Sequence
<220> FEATURE:
<223> OTHER INFORMATION: primer HvAP2-acti-C3

<400> SEQUENCE: 31
ctgcaggcag gtcgaagtgg tcatcg                                         26

<210> SEQ ID NO 32
<211> LENGTH: 26
<212> TYPE: DNA
<213> ORGANISM: Artificial Sequence
<220> FEATURE:
<223> OTHER INFORMATION: primer HvAP2-acti-N1

<400> SEQUENCE: 32
gaattcgagg acttcgatga ccactt                                         26

<210> SEQ ID NO 33
<211> LENGTH: 26
<212> TYPE: DNA
<213> ORGANISM: Artificial Sequence
<220> FEATURE:
<223> OTHER INFORMATION: primer HvAP2-acti-N2

<400> SEQUENCE: 33
gaattcgagc tgatggagtt tttcaa                                         26

<210> SEQ ID NO 34
<211> LENGTH: 25
<212> TYPE: DNA
<213> ORGANISM: Artificial Sequence
<220> FEATURE:
<223> OTHER INFORMATION: primer HvAP2-acti-N3

<400> SEQUENCE: 34
gaattcgccc tcagcgtgga cagtg                                          25

<210> SEQ ID NO 35
<211> LENGTH: 14
<212> TYPE: PRT
<213> ORGANISM: Hordeum vulgare
<220> FEATURE:
<221> NAME/KEY: DOMAIN
<222> LOCATION: (1)..(14)
<223> OTHER INFORMATION: transcriptional activation domain

<400> SEQUENCE: 35

Ala Leu Ser Val Asp Ser Gly Met Asp Ala Val Ser Leu Trp
 1               5                  10

<210> SEQ ID NO 36
<211> LENGTH: 42
<212> TYPE: DNA
<213> ORGANISM: Hordeum vulgare
```

-continued

```
<400> SEQUENCE: 36
gccctcagcg tggacagtgg catggacgcc gtcagcctct gg                         42

<210> SEQ ID NO 37
<211> LENGTH: 21
<212> TYPE: DNA
<213> ORGANISM: Artificial Sequence
<220> FEATURE:
<223> OTHER INFORMATION: sense primer PDF1.2

<400> SEQUENCE: 37
atggctaagt tgcttccat c                                                 21

<210> SEQ ID NO 38
<211> LENGTH: 21
<212> TYPE: DNA
<213> ORGANISM: Artificial Sequence
<220> FEATURE:
<223> OTHER INFORMATION: antisense primer PDF1.2

<400> SEQUENCE: 38
aatacacacc atttagcacc a                                                21

<210> SEQ ID NO 39
<211> LENGTH: 21
<212> TYPE: DNA
<213> ORGANISM: Artificial Sequence
<220> FEATURE:
<223> OTHER INFORMATION: sense primer PR1

<400> SEQUENCE: 39
atgaatttta ctggctattc t                                                21

<210> SEQ ID NO 40
<211> LENGTH: 21
<212> TYPE: DNA
<213> ORGANISM: Artificial Sequence
<220> FEATURE:
<223> OTHER INFORMATION: antisense primer PR1

<400> SEQUENCE: 40
gtatggcttc tcgttcacat a                                                21

<210> SEQ ID NO 41
<211> LENGTH: 25
<212> TYPE: DNA
<213> ORGANISM: Artificial Sequence
<220> FEATURE:
<223> OTHER INFORMATION: sense primer AtRP5

<400> SEQUENCE: 41
ccagtattca cattctcttc ttcgt                                            25

<210> SEQ ID NO 42
<211> LENGTH: 25
<212> TYPE: DNA
<213> ORGANISM: Artificial Sequence
<220> FEATURE:
<223> OTHER INFORMATION: antisense primer AtRP5

<400> SEQUENCE: 42
gtggttttat cccatctttt acatt                                            25

<210> SEQ ID NO 43
<211> LENGTH: 20
<212> TYPE: DNA
```

<213> ORGANISM: Artificial Sequence
<220> FEATURE:
<223> OTHER INFORMATION: sense primer COR6.6

<400> SEQUENCE: 43
tgagaggaga agagcaatgt					20

<210> SEQ ID NO 44
<211> LENGTH: 21
<212> TYPE: DNA
<213> ORGANISM: Artificial Sequence
<220> FEATURE:
<223> OTHER INFORMATION: antisens primer COR6.6

<400> SEQUENCE: 44
tgtccttcac gaagttaaca c					21

<210> SEQ ID NO 45
<211> LENGTH: 25
<212> TYPE: DNA
<213> ORGANISM: Artificial Sequence
<220> FEATURE:
<223> OTHER INFORMATION: sense primer GSH1

<400> SEQUENCE: 45
gaatgggaaa aagtaatgga aggtg				25

<210> SEQ ID NO 46
<211> LENGTH: 25
<212> TYPE: DNA
<213> ORGANISM: Artificial Sequence
<220> FEATURE:
<223> OTHER INFORMATION: antisens primer GSH1

<400> SEQUENCE: 46
ctctgggaat attgttgtca gatgg				25

<210> SEQ ID NO 47
<211> LENGTH: 334
<212> TYPE: PRT
<213> ORGANISM: Oryza sativa

<400> SEQUENCE: 47

Met Cys Gly Gly Ala Ile Leu Ala Glu Phe Ile Pro Ala Pro Ser Arg
 1               5                  10                  15

Ala Ala Ala Ala Thr Lys Arg Val Thr Ala Ser His Leu Trp Pro Ala
                 20                  25                  30

Gly Ser Lys Asn Ala Ala Arg Gly Lys Ser Lys Ser Lys Arg Gln Gln
             35                  40                  45

Arg Ser Phe Ala Asp Val Asp Asp Phe Glu Ala Ala Phe Glu Gln Phe
         50                  55                  60

Asp Asp Asp Ser Asp Phe Asp Asp Ala Glu Glu Glu Asp Glu Gly His
65                  70                  75                  80

Phe Val Phe Ala Ser Lys Ser Arg Val Val Ala Gly His Asp Gly Arg
                 85                  90                  95

Ala Ala Ala Arg Ala Ala Ser Lys Lys Lys Arg Gly Arg His Phe Arg
            100                 105                 110

Gly Ile Arg Gln Arg Pro Trp Gly Lys Trp Ala Ala Glu Ile Arg Asp
        115                 120                 125

Pro His Lys Gly Thr Arg Val Trp Leu Gly Thr Phe Asn Thr Pro Glu
    130                 135                 140

Glu Ala Ala Arg Ala Tyr Asp Val Glu Ala Arg Arg Leu Arg Gly Ser

-continued

```
145                 150                 155                 160
Lys Ala Lys Val Asn Phe Pro Ala Thr Pro Ala Ala Arg Pro Arg
                165                 170                 175
Arg Gly Asn Thr Arg Ala Thr Ala Val Pro Pro Ala Thr Ala Pro
            180                 185                 190
Ala Ala Ala Pro Pro Arg Gly Leu Lys Arg Glu Phe Ser Pro Pro Ala
        195                 200                 205
Glu Thr Ala Leu Pro Phe Phe Thr Asn Gly Phe Val Asp Leu Thr Thr
        210                 215                 220
Ala Ala Ala Pro Pro Pro Ala Met Met Met Thr Ser Ser Phe Thr Asp
225                 230                 235                 240
Ser Val Ala Thr Ser Glu Ser Gly Gly Ser Pro Ala Lys Lys Ala Arg
            245                 250                 255
Ser Asp Asp Val Asp Ser Ser Glu Gly Ser Val Gly Gly Gly Ser Asp
            260                 265                 270
Thr Leu Gly Phe Thr Asp Glu Leu Glu Phe Asp Pro Phe Met Leu Phe
            275                 280                 285
Gln Leu Pro Tyr Ser Asp Gly Tyr Glu Ser Ile Asp Ser Leu Phe Ala
            290                 295                 300
Ala Gly Asp Ala Asn Ser Ala Asn Thr Asp Met Asn Ala Gly Val Asn
305                 310                 315                 320
Leu Trp Ser Phe Asp Asp Phe Pro Ile Asp Gly Ala Leu Phe
                325                 330
```